(12) United States Patent
Walker et al.

(10) Patent No.: US 6,974,574 B2
(45) Date of Patent: Dec. 13, 2005

(54) METHODS OF INDUCING AN HIV SPECIFIC RESPONSE USING A VPR-SPECIFIC EPITOPE

(75) Inventors: Bruce D. Walker, Milton, MA (US); Marcus Altfeld, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/222,463

(22) Filed: Aug. 16, 2002

(65) Prior Publication Data

US 2003/0219450 A1 Nov. 27, 2003

Related U.S. Application Data

(60) Provisional application No. 60/313,208, filed on Aug. 17, 2001, and provisional application No. 60/313,408, filed on Aug. 16, 2001.

(51) Int. Cl.[7] .............................................. A61K 39/00
(52) U.S. Cl. ................................ 424/192.1; 424/185.1; 424/188.1; 424/196.11; 424/202.1; 424/208.1; 530/350; 530/328; 530/826
(58) Field of Search ................................ 530/350, 328, 530/826; 424/185.1, 188.1, 192.1, 196.11, 202.1, 208.1

(56) References Cited

U.S. PATENT DOCUMENTS

| | | | |
|---|---|---|---|
| 6,193,981 B1 * | 2/2001 | Goldstein ................. | 424/208.1 |
| 6,340,461 B1 | 1/2002 | Terman ..................... | 424/193.1 |
| 6,413,517 B1 | 7/2002 | Sette et al. ............... | 424/185.1 |
| 6,534,482 B1 | 3/2003 | Fikes et al. .................... | 514/44 |

FOREIGN PATENT DOCUMENTS

| WO | WO 97/34621 | 9/1997 |
|---|---|---|
| WO | WO 99/58658 | 11/1999 |

OTHER PUBLICATIONS

Choppin et al. "HLA–binding regions of HIV–1 proteins. II. A systematic study of viral proteins" Journal of immunology (Baltimore, Md. :1950), vol. 147, No. 2 (Jul. 15, 1991), pp. 575–583.*

Sarobe et al. "Induction of neutralizing antibodies against human immunodeficiency virus type 1 using synthetic peptide constructs containing an immunodominant T–helper cell determinant from vpr", Journal of acquired immune deficiency syndromes, vol. 7, No.*

Myers et al. "Human Retroviruses and AIDS, 1991" published by Theoretical Biology and Biophysic Los Alamos National Laboratory, p. II–59.*

Addo, et al., *Proc. Natl. Acad. Sci. USA*, 98(4):1781–1786 (2001).

Allen, et al., *Nature*, 407:386–390 (2000).

Altfeld, et al., *J. Immunol.*, 167:2743–2752 (2001).

Altfeld, et al., *J. Virol.*, 75(3):1301–1311 (2001).

Altfeld, et al., *J. Virol.*, 74(18):8541–8549 (2000).

Altfeld, et al., *J. Exp. Med.*, 193(2):169–180(2001).

Altfeld, et al., *Curr. Op. Immunol.*, 12:375–380 (2000).

Borman, et al., *J. Virol.*, 69(4):2058–2067 (1995).

Boyce, et al., *Virus Genes*, 19(1):15–22 (1999).

Brander, et al., *J. Clin. Invest.*, 101:2559–2566 (1998).

Brander, et al., *Curr. Op. Immunol.*, 11:451–459 (1999).

Brosterhus, et al., *Eur. J. Immunol.*, 29(12):4053–4059 (1999).

(Continued)

*Primary Examiner*—Jeffrey Stucker
(74) *Attorney, Agent, or Firm*—Ingrid A. Beattie; Mintz, Levin

(57) ABSTRACT

The invention features an immunogenic composition containing a frequently-recognized epitope of an HIV-1 accessory protein such as Vpr and methods of inducing an immune response using such an epitope. The epitope peptide contains the amino acid sequence ALIRILQQL of a functionally active domain or a structural domain of the accessory protein.

3 Claims, 8 Drawing Sheets

| Overlapping Peptides (n = 388) | SFC / Million PBMC 300 600 900 1200 1500 1800 | |
|---|---|---|
| none | | p15 Gag |
| MEKIRLRPGGKKKYK (SEQ ID NO : 6) | ▬▬▬ | p17 Gag |
| LEEMMTACQGVGGPGHKARV (SEQ ID NO : 18) | ▬▬ | p24 Gag |
| SQIYPGIKVRQLCKL (SEQ ID NO : 19)<br>WKGSPAIFQSSMTKI (SEQ ID NO : 20) | ▬<br>▬ | RT |
| HIPRRIRQGLERALL (SEQ ID NO : 21) | ▬▬▬ | gp41 Env |
| none | | gp120 Env |
| PQVPLRRMTYKAAVDLSHFL (SEQ ID NO : 22)<br>KAAVDLSHFLKEKGGLEGLI (SEQ ID NO : 23)<br>EEEEVGFPVTPQVPLRPMTY (SEQ ID NO : 24) | ▬<br>▬<br>▬▬ | Nef |
| none | | Rev |
| none | | Tat |
| VRHFPRIWLHGLGQH (SEQ ID NO : 25) | ▬ | Vpr |
| none | | Vpu |
| RIRTWKSLVKHHMYI (SEQ ID NO : 26)<br>THPRVSSEVHIPLG (SEQ ID NO : 27) | ▬▬<br>▬▬ | Vif |

OTHER PUBLICATIONS

Bunce, et al., *Tissue Antigens*, 45(2):81–90 (1995).
Camaur, et al., *J. Virol.*, 70(9):6106–6111 (1996).
Chen, et al., *J. Virol.*, 73(4):3236–3245 (1999).
Cosimi, et al., "The Characterization of HIV–1 Specific CD4+ T Helper Epitopes", http://hiv–web.lanl.gov/REVIEWS/Cosimi.html, 8 pages.
Cullen, B.R., *Cell*, 93(5):685–692 (1998).
Desrosiers, et al., *J. Virol.*, 72(2):1431–1437 (1998).
DiBrino, et al., *Proc. Natl. Acad. Sci. USA*, 90:1508–1512 (1993).
Emerman, et al., *Science*, 280:1880–1884 (1998).
Fouchier, et al., *J. Virol.*, 72(7):6004–6013 (1998).
Fouchier, et al., *Advances in Virus Research*, 52:275–299 (1999).
Frankel, et al., *Annu. Rev. Biochem.*, 67:1–25 (1998).
Gabuzda, et al., *J. Acquir. Immune Defic. Syndr.*, 7(9):908–915 (1994).
Gabuzda, et al., *J. Virol.*, 66(11):6489–6495 (1992).
Gibbs, et al., *J. Virol.*, 69(4):2378–2383 (1995).
Goulder, et al., *J. Virol.*, 75(3):1339–1347 (2001).
Goulder, et al., *J. Virol.*, 74(12):5679–5690 (2000).
Goulder, et al., *J. Exp. Med.*, 185(8):1423–1433 (1997).
Goulder, et al., *J. Exp. Med.*, 192(12):1819–1831 (2000).
Goulder, et al., *AIDS*, 13(suppl. A):S121–S136 (1999).
Goulder, P.J., *Annals of the New York Academy of Sciences*, 918:330–345 (2000).
Heinzinger, et al., *Proc. Natl. Acad. Sci. USA*, 91:7311–7315 (1994).
Johnson, et al., *J. Immunol.*, 147(5):1512–1521 (1991).
Kamata, et al., *J. Virol.*, 74(15):7179–7186 (2000).
Lai, et al., *FEBS Letters*, 469:191–195 (2000).
Lang, et al., *J. Virol.*, 67(2):902–912 (1993).
Mahalingam, et al., *Virology*, 207:297–302 (1995).
Mahalingam, et al., *J. Virol.*, 71(9):6339–6347 (1997).
Marzio, et al., *J. Virol.*, 69(12):7909–7916 (1995).
McMichael, et al., *Nature*, 410:980–987 (2001).
Nie, et al., *J. Virol.*, 72(5):4104–4115 (1998).
Nietfeld, et al., *J. Immunol.*, 154(5):2188–2197 (1995).
Nishizawa, et al., *Virology*, 263(2):313–322 (1999).
Pitcher, et al., *Nat. Med.*, 5(5):518–525 (1999).
Plata, et al., *Nature*, 328:348–351 (1987).
Poon, et al., *Science*, 281:266–269 (1998).
Rammensee, et al., *Immunogenetics*, 41(4):178–228 (1995).
Rogel, et al., *J. Virol.*, 69(2):882–888 (1995).
Rosenberg, et al., *Nature*, 407:523–526 (2000).
Sakai, et al., *Virus Genes*, 18(2):179–181 (1999).
Scheffold, et al., *Eur. Cytokine Netw.*, 9(suppl. No. 3):5–11 (1998).
Simon, et al., *J. Virol.*, 73(4):2675–2681 (1999).
Simon, et al., *J. Virol.*, 71(7):5259–5267 (1997).
Trono, D., *Cell*, 82(2):189–192 (1995).
Trono, D., *Nature*, 4(12):1368–1369 (1998).
von Schwedler, et al., *J. Virol.*, 67(8):4945–4955 (1993).
Walker, et al., *Nature*, 407:313–314 (2000).
Walker, et al., *Nature*, 328:345–348 (1987).
Walker, et al., *Proc. Natl. Acad. Sci. USA*, 86(23):9514–9518 (1989).
Yang, et al., *J. Biol. Chem.*, 276(7):4889–4893 (2001).
Zhang, et al., *J. Virol.*, 74(18):8252–8261 (2000).

* cited by examiner

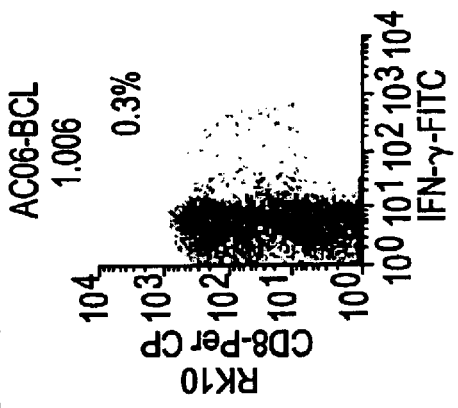
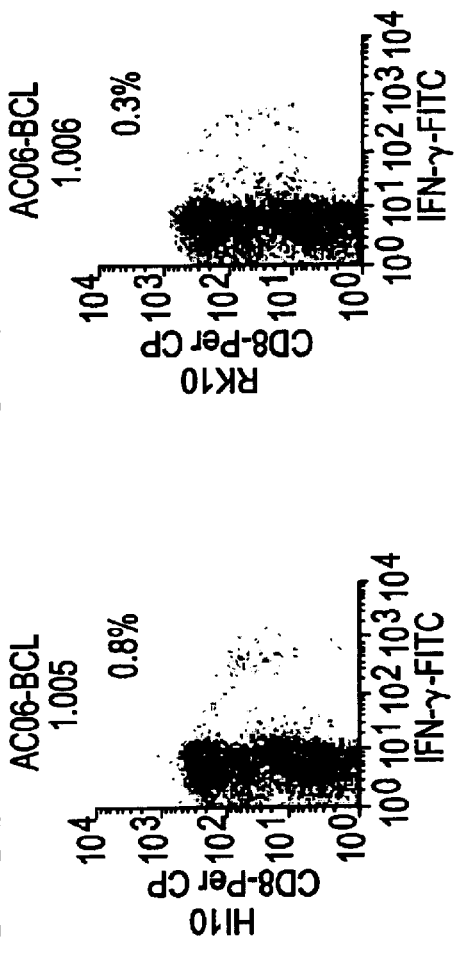
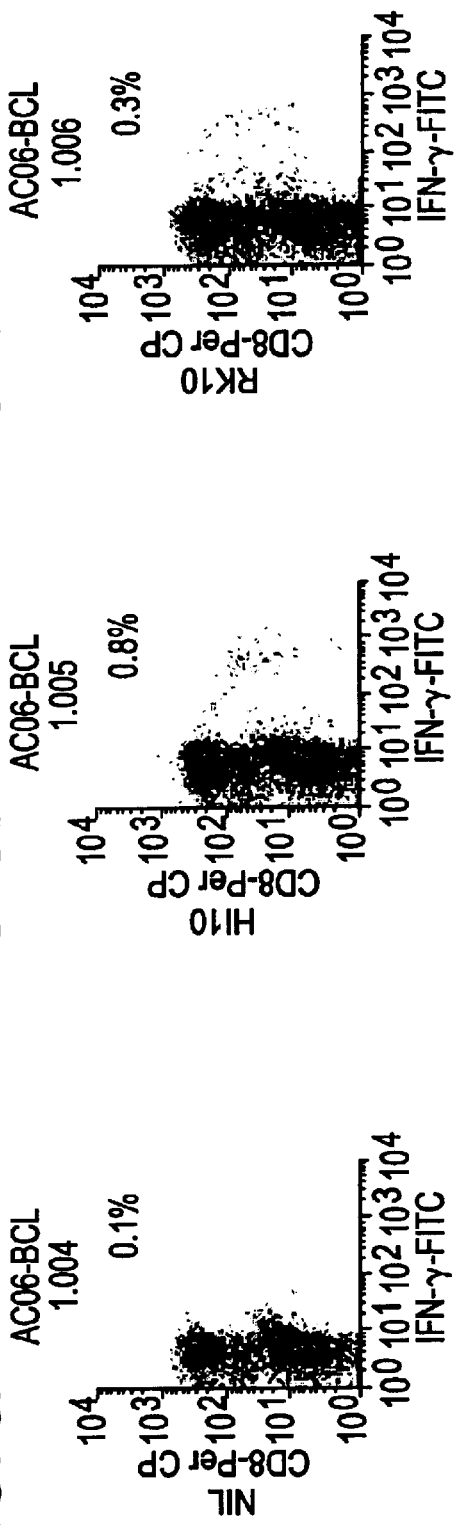
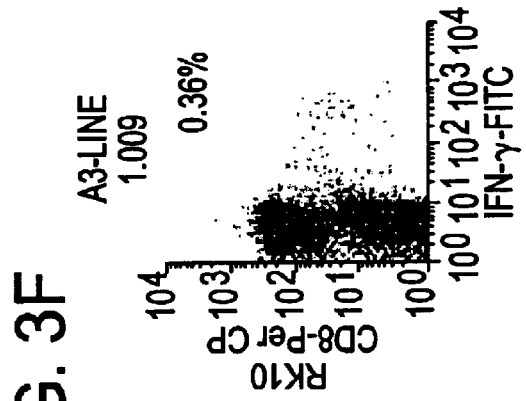
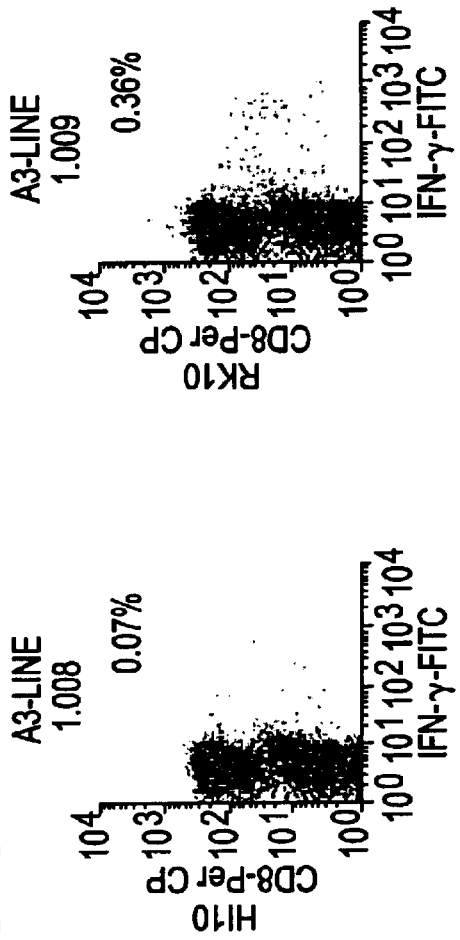
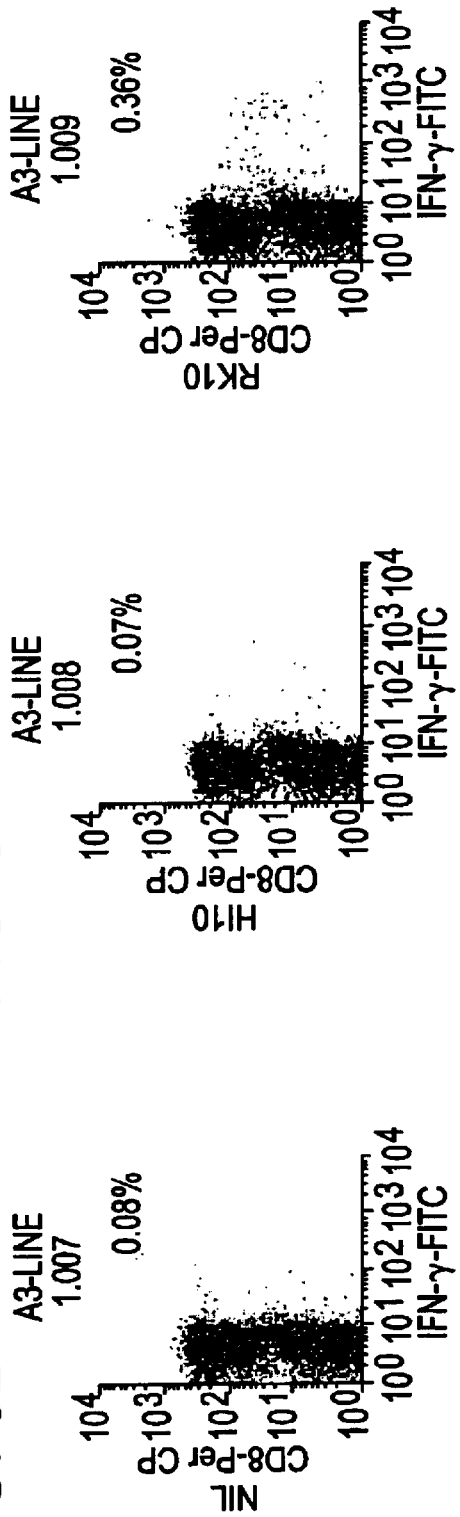

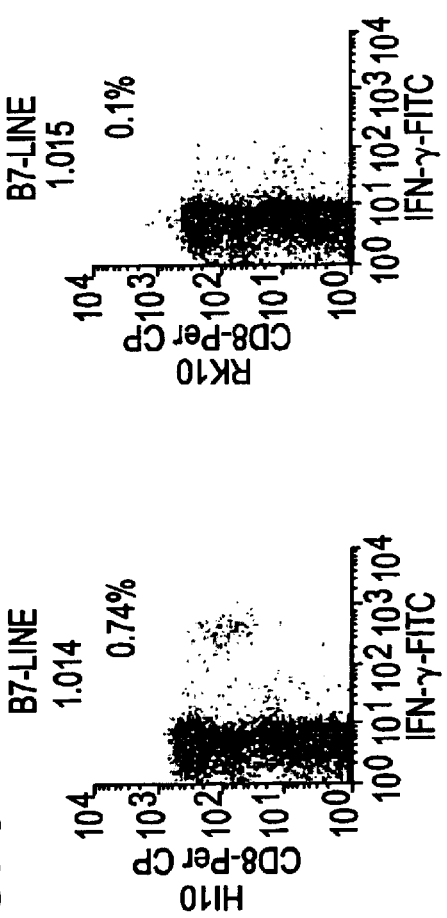
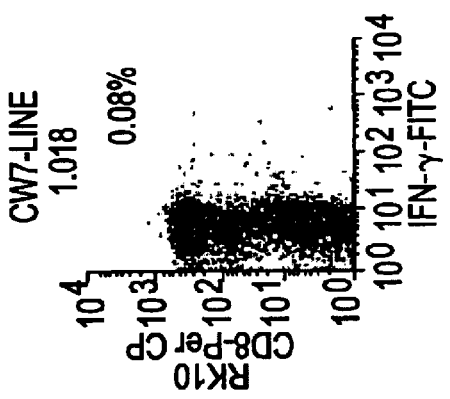
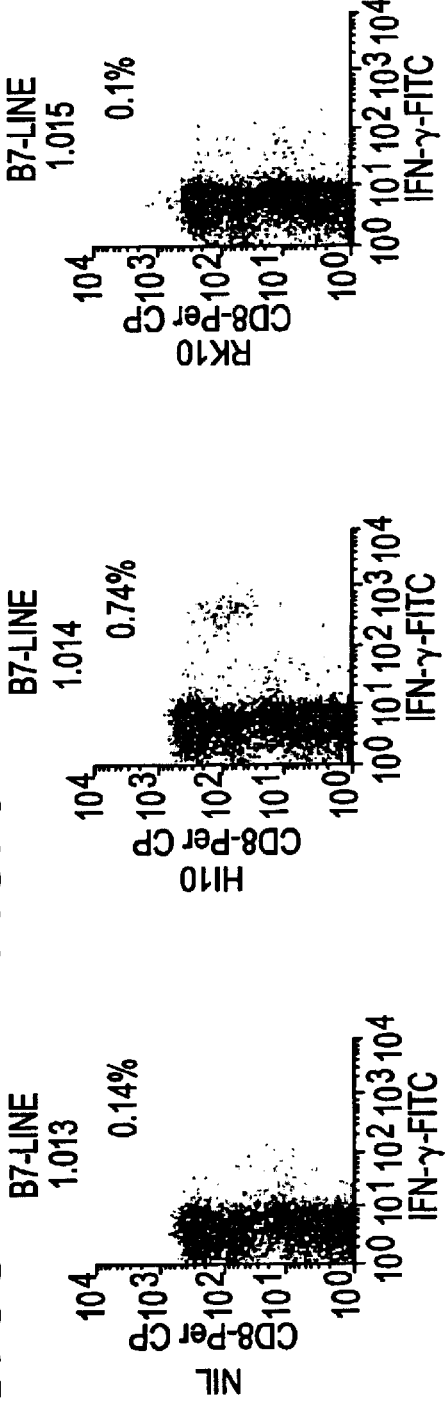
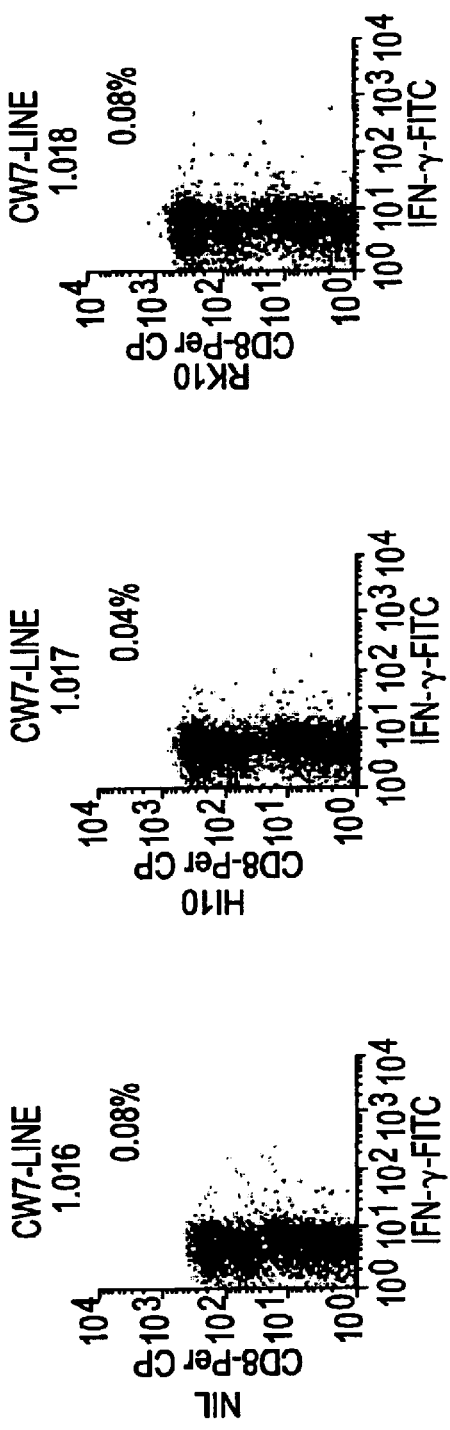

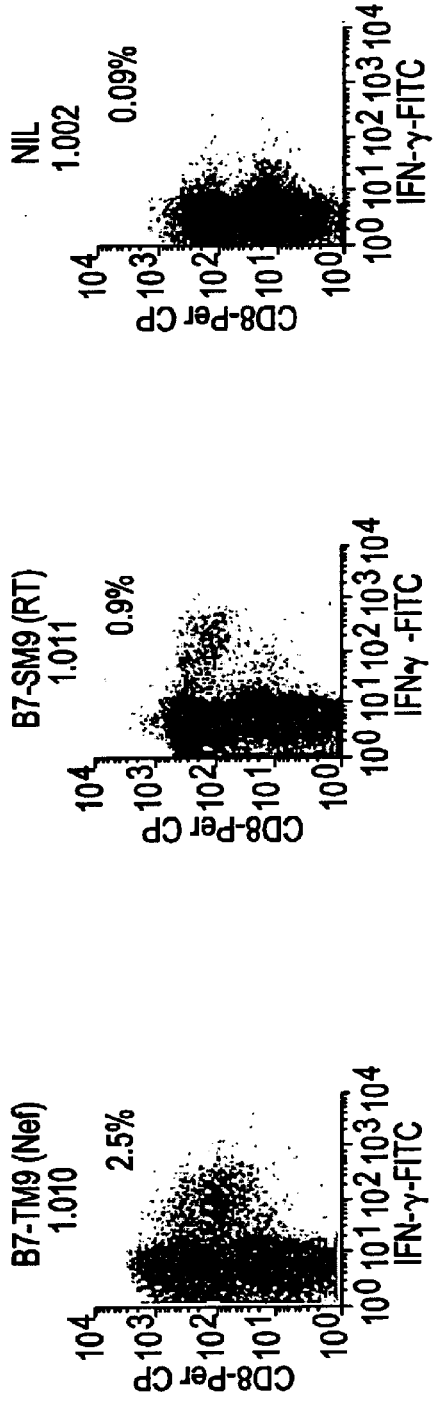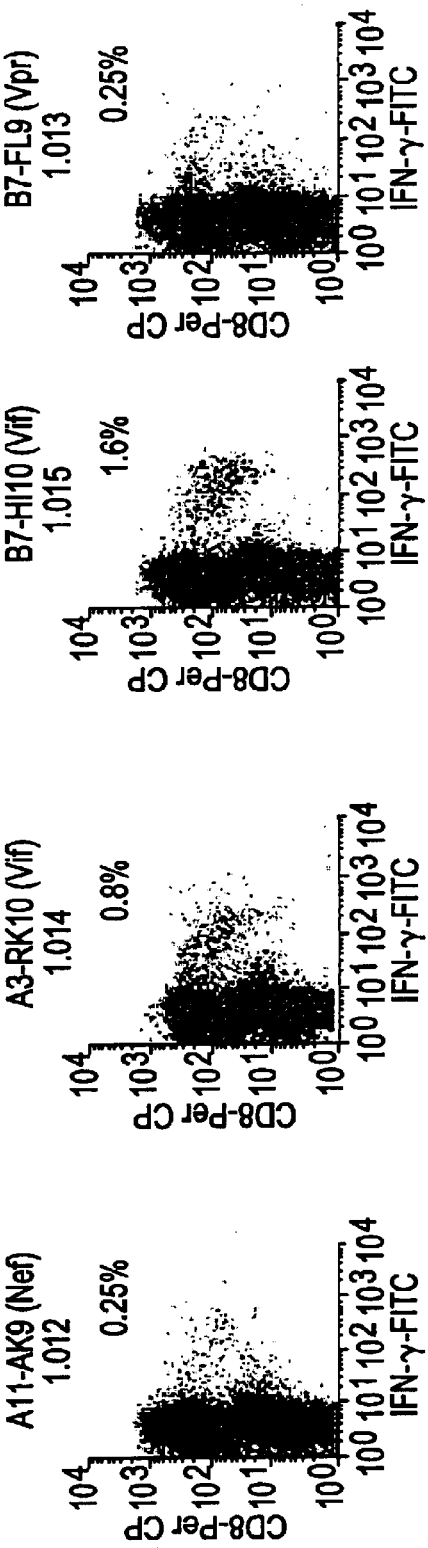

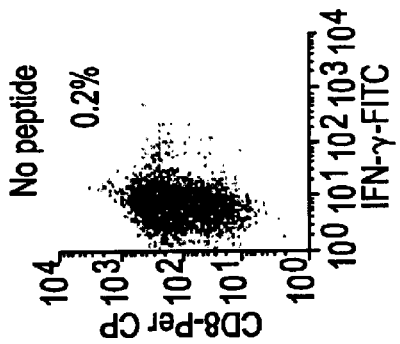
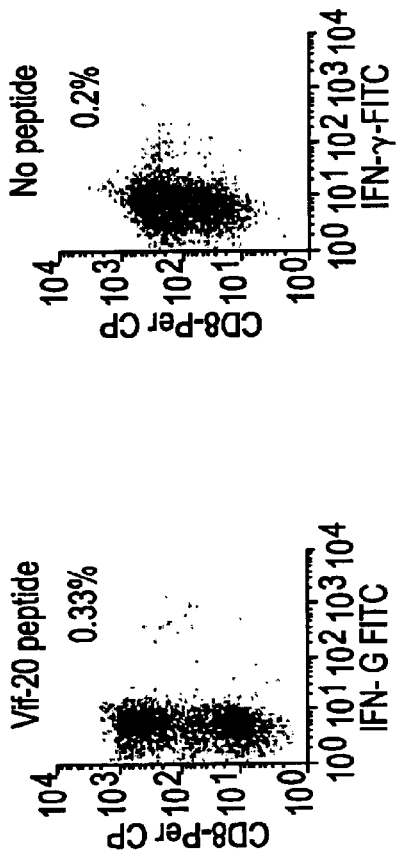
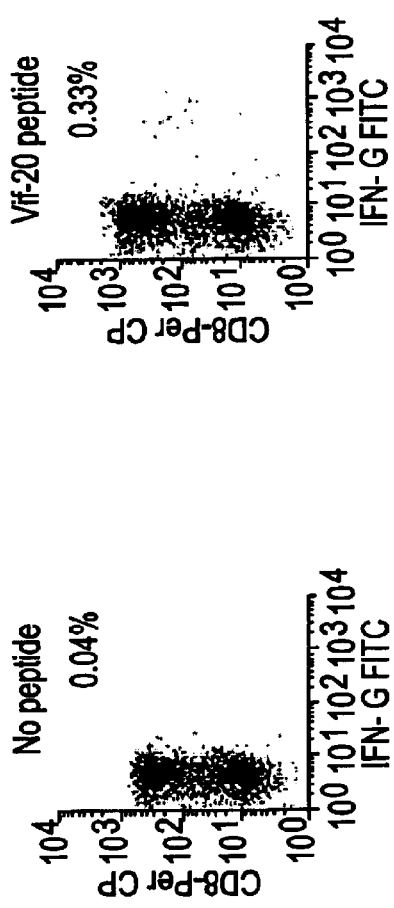
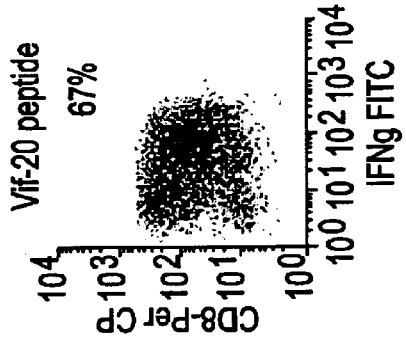
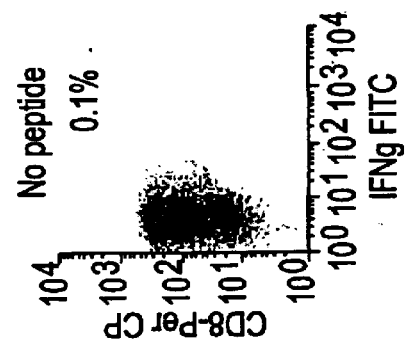
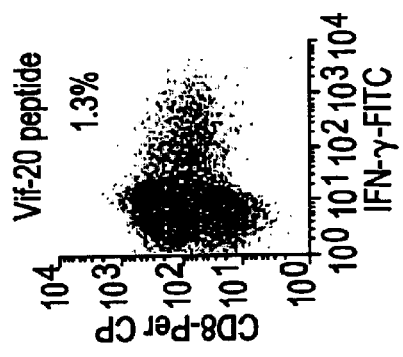

SEQUENCE LISTING

```
<160> NUMBER OF SEQ ID NOS: 27
<210> SEQ ID NO 1
<211> LENGTH: 9
<212> TYPE: PRT
<213> ORGANISM: Human immunodeficiency virus type 1

<400> SEQUENCE: 1

Ala Ile Ile Arg Ile Leu Gln Gln Leu
 1               5

<210> SEQ ID NO 2
<211> LENGTH: 9
<212> TYPE: PRT
<213> ORGANISM: Human immunodeficiency virus type 1

<400> SEQUENCE: 2

Ala Leu Ile Arg Ile Leu Gln Gln Leu
 1               5

<210> SEQ ID NO 3
<211> LENGTH: 10
<212> TYPE: PRT
<213> ORGANISM: Human immunodeficiency virus type 1

<400> SEQUENCE: 3

Arg Ile Arg Thr Trp Lys Ser Leu Val Lys
```

-continued

```
<210> SEQ ID NO 4
<211> LENGTH: 10
<212> TYPE: PRT
<213> ORGANISM: Human immunodeficiency virus type 1

<400> SEQUENCE: 4

His Pro Arg Val Ser Ser Glu Val His Ile
  1               5                  10

<210> SEQ ID NO 5
<211> LENGTH: 14
<212> TYPE: PRT
<213> ORGANISM: Human immunodeficiency virus type 1

<400> SEQUENCE: 5

Thr His Pro Arg Val Ser Ser Glu Val His Ile Pro Leu Gly
  1               5                  10

<210> SEQ ID NO 6
<211> LENGTH: 15
<212> TYPE: PRT
<213> ORGANISM: Human immunodeficiency virus type 1

<400> SEQUENCE: 6

Trp Glu Lys Ile Arg Leu Arg Pro Gly Gly Lys Lys Lys Tyr Lys
  1               5                  10                  15

<210> SEQ ID NO 7
<211> LENGTH: 9
<212> TYPE: PRT
<213> ORGANISM: Human immunodeficiency virus type 1

<400> SEQUENCE: 7

Gly Pro Gly His Lys Ala Arg Val Leu
  1               5

<210> SEQ ID NO 8
<211> LENGTH: 9
<212> TYPE: PRT
<213> ORGANISM: Human immunodeficiency virus type 1

<400> SEQUENCE: 8

Ser Leu Tyr Asn Thr Val Ala Thr Leu
  1               5

<210> SEQ ID NO 9
<211> LENGTH: 9
<212> TYPE: PRT
<213> ORGANISM: Human immunodeficiency virus type 1

<400> SEQUENCE: 9

Phe Pro Arg Ile Trp Leu His Gly Leu
  1               5

<210> SEQ ID NO 10
<211> LENGTH: 9
<212> TYPE: PRT
<213> ORGANISM: Human immunodeficiency virus type 1

<400> SEQUENCE: 10

Arg Glu Pro His Asn Glu Trp Thr Leu
  1               5
```

```
<210> SEQ ID NO 11
<211> LENGTH: 9
<212> TYPE: PRT
<213> ORGANISM: Human immunodeficiency virus type 1

<400> SEQUENCE: 11

Ala Val Arg His Phe Pro Arg Ile Trp
 1               5

<210> SEQ ID NO 12
<211> LENGTH: 9
<212> TYPE: PRT
<213> ORGANISM: Human immunodeficiency virus type 1

<400> SEQUENCE: 12

Ile Ser Lys Lys Ala Lys Gly Trp Phe
 1               5

<210> SEQ ID NO 13
<211> LENGTH: 10
<212> TYPE: PRT
<213> ORGANISM: Human immunodeficiency virus type 1

<400> SEQUENCE: 13

Leu Ala Asp Gln Leu Ile His Leu His Tyr
 1               5                  10

<210> SEQ ID NO 14
<211> LENGTH: 11
<212> TYPE: PRT
<213> ORGANISM: Human immunodeficiency virus type 1

<400> SEQUENCE: 14

Met Arg Ile Arg Thr Trp Lys Ser Leu Val Lys
 1               5                  10

<210> SEQ ID NO 15
<211> LENGTH: 11
<212> TYPE: PRT
<213> ORGANISM: Human immunodeficiency virus type 1

<400> SEQUENCE: 15

Arg Ile Arg Thr Trp Lys Ser Leu Val Lys His
 1               5                  10

<210> SEQ ID NO 16
<211> LENGTH: 11
<212> TYPE: PRT
<213> ORGANISM: Human immunodeficiency virus type 1

<400> SEQUENCE: 16

Thr His Pro Arg Val Ser Ser Glu Val His Ile
 1               5                  10

<210> SEQ ID NO 17
<211> LENGTH: 11
<212> TYPE: PRT
<213> ORGANISM: Human immunodeficiency virus type 1

<400> SEQUENCE: 17

His Pro Arg Val Ser Ser Glu Val His Ile Pro
 1               5                  10

<210> SEQ ID NO 18
```

```
<211> LENGTH: 20
<212> TYPE: PRT
<213> ORGANISM: Human immunodeficiency virus type 1

<400> SEQUENCE: 18

Leu Glu Glu Met Met Thr Ala Cys Gln Gly Val Gly Gly Pro Gly His
 1               5                  10                  15

Lys Ala Arg Val
            20

<210> SEQ ID NO 19
<211> LENGTH: 15
<212> TYPE: PRT
<213> ORGANISM: Human immunodeficiency virus type 1

<400> SEQUENCE: 19

Ser Gln Ile Tyr Pro Gly Ile Lys Val Arg Gln Leu Cys Lys Leu
 1               5                  10                  15

<210> SEQ ID NO 20
<211> LENGTH: 15
<212> TYPE: PRT
<213> ORGANISM: Human immunodeficiency virus type 1

<400> SEQUENCE: 20

Trp Lys Gly Ser Pro Ala Ile Phe Gln Ser Ser Met Thr Lys Ile
 1               5                  10                  15

<210> SEQ ID NO 21
<211> LENGTH: 15
<212> TYPE: PRT
<213> ORGANISM: Human immunodeficiency virus type 1

<400> SEQUENCE: 21

His Ile Pro Arg Arg Ile Arg Gln Gly Leu Glu Arg Ala Leu Leu
 1               5                  10                  15

<210> SEQ ID NO 22
<211> LENGTH: 20
<212> TYPE: PRT
<213> ORGANISM: Human immunodeficiency virus type 1

<400> SEQUENCE: 22

Pro Gln Val Pro Leu Arg Arg Met Thr Tyr Lys Ala Ala Val Asp Leu
 1               5                  10                  15

Ser His Phe Leu
            20

<210> SEQ ID NO 23
<211> LENGTH: 20
<212> TYPE: PRT
<213> ORGANISM: Human immunodeficiency virus type 1

<400> SEQUENCE: 23

Lys Ala Ala Val Asp Leu Ser His Phe Leu Lys Glu Lys Gly Gly Leu
 1               5                  10                  15

Glu Gly Leu Ile
            20

<210> SEQ ID NO 24
<211> LENGTH: 20
<212> TYPE: PRT
<213> ORGANISM: Human immunodeficiency virus type 1
```

-continued

```
<400> SEQUENCE: 24

Glu Glu Glu Glu Val Gly Phe Pro Val Thr Pro Gln Val Pro Leu Arg
1               5                   10                  15

Pro Met Thr Tyr
            20

<210> SEQ ID NO 25
<211> LENGTH: 15
<212> TYPE: PRT
<213> ORGANISM: Human immunodeficiency virus type 1

<400> SEQUENCE: 25

Val Arg His Phe Pro Arg Ile Trp Leu His Gly Leu Gly Gln His
1               5                   10                  15

<210> SEQ ID NO 26
<211> LENGTH: 15
<212> TYPE: PRT
<213> ORGANISM: Human immunodeficiency virus type 1

<400> SEQUENCE: 26

Arg Ile Arg Thr Trp Lys Ser Leu Val Lys His His Met Tyr Ile
1               5                   10                  15

<210> SEQ ID NO 27
<211> LENGTH: 14
<212> TYPE: PRT
<213> ORGANISM: Human immunodeficiency virus type 1

<400> SEQUENCE: 27

Thr His Pro Arg Val Ser Ser Glu Val His Ile Pro Leu Gly
1               5                   10
```

METHODS OF INDUCING AN HIV SPECIFIC RESPONSE USING A VPR-SPECIFIC EPITOPE

This application claims priority to provisional patent application U.S. Ser. No. 60/313,408, filed Aug. 16, 2001, and provisional patent application U.S. Ser. No. 60/313,208, filed on Aug. 17, 2001. The entire contents of each application is hereby incorporated by reference.

STATEMENT AS TO FEDERALLY SPONSORED RESEARCH

This invention was made with U.S. Government support under National Institutes of Health grants R37 AI128568, R01AI30914, RO1 AI 44656, RO1 AI 40873, UO1 AI41535, and UO1 AI41531. The government has certain rights in the invention.

BACKGROUND OF THE INVENTION

The invention relates to immunity to T cell immunity to viral antigens.

Human Immunodeficiency Virus-1 (HIV-1) has infected over 57 million and killed over 22 million individuals worldwide since the beginning of the epidemic. More than 95% of HIV-1 infected individuals live in developing countries and have no access to antiretroviral treatment.

HIV-1 specific cytotoxic T lymphocytes (CTL) and T helper cells play a central role in controlling viral replication. Analysis of HIV-1-specific immunity has largely focused on assessment of immune responses directed against the structural HIV-1 proteins Gag, Pol and Env, as well as the accessory protein Nef. Recent data suggest that CTL responses directed against the early expressed regulatory proteins Tat and Rev also play a central role in the HIV-1-specific immune response. Despite advances in knowledge regarding HIV-1-specific immunity, the need for an effective vaccine remains great.

SUMMARY OF THE INVENTION

The invention provides improved vaccines, which elicit a CTL response against HIV-1. The vaccines contain a peptide (or nucleic acid encoding the peptide) derived from an HIV-1 accessory protein such as Vpr or Vif. Accessory proteins include Tat (transactivator of transcription), Rev (regulates late gene expression), Vif (viral infectivity), Vpu (influences viral release), Vpr, Nef (negative regulator of transcription).

Optionally, the vaccine contains peptides derived from other HIV-1 proteins, e.g., structural proteins such as Gag, Pol, or Env. The vaccines may also contain peptides derived from other accessory proteins such as Nef. Preferably, the composition does not contain a Vpu-derived peptide. Preferably, the vaccine contains an optimal CTL epitope. For example, the vaccine contains a Vpr epitope, which is located within alpha helix Hα2 of Vpr (e.g., a peptide containing the amino acid sequence AIIRILQQL (SEQ ID NO:1) or ALIRILQQL (SEQ ID NO:2). Preferably, the epitope is derived from a functionally active domain or structural domain of the protein from which the epitope is derived.

Accordingly, the invention encompasses an immunogenic composition, which contains a frequently-recognized epitope of an HIV-1 accessory protein, e.g., Tat, Rev, Vif, Vpu, Vpr, or Nef. A frequently-recognized epitope is an epitope to which an immune response is generated by a greater proportion of individuals with long-term non-progressive HIV infection compared to acute infection. For example, individuals with long-term non-progressive or chronic viral infections targettted Vpr epitopes more frequently than individuals with acute viral infection. Frequency of recognition is measured using a standard ELISPOT assay. A frequently-recognized epitope is characterized as one having a magnitude of response greater than approximately 25 SFC/Mill PBMC. For example, a frequently-recognized epitope has a magnitude of CTL response that is at least 2-fold, 5-fold, 10-fold, 25-fold, 50-fold or more compared to the magnitude of CTL response of an HIV-1-negative control individual. Similarly, a frequently-recognized epitope is one characterized by the ability to induce a CTL response in a population of PBMCs obtained from long-term non-progressive HIV-1 individuals that is at least 10%, 20%, 50%, 75%, 100%, 200% or more compared to the magnitude of a CTL response induced in a population of PBMCs obtained from an individual with an acute viral infection.

The epitope contains an amino acid sequence of a functionally active domain or a structural domain of the accessory protein. HIV-1 Viral Protein R (Vpr) is predominantly localized to the nucleus and plays an important role for the viral preintegration complex import into the nucleus. Preferably, the protein is Vpr and the structural domain contains an alpha helix Hα2 of Vpr. The functionally active domain is preferably a perinuclear localization domain. One advantage of the immunogenic compositions is that epitopes derived from structural or functionally active domains are less variable with respect to amino acid sequence among clinical isolates and over the course of HIV-1 infection. Examples of such epitopes include the Vpr peptides containing amino acid sequences of SEQ ID NO:1, 2, 3, 4, 9, 10, 11, 12, or 13. An epitope containing the amino acid sequence of ALIRILAAL (SEQ ID NO:2) is a more potent immunogen compared to a SEQ ID NO:1. Examples of Vif peptides include epitope peptides with amino acid sequences SEQ ID NO:3, 4, 12, and 13, 26, or 27. Optionally, the composition contains a mixture of accessory protein peptides (e.g., epitopes derived from at least two accessory proteins such as Vpr and Vif). In some embodiments, the composition does not contain a Vpu polypeptide.

A method of inducing an HIV-1 specific cytotoxic T cell immune response is carried out by contacting a CD8+ T cell with a polypeptide containin an epitope of an HIV-1 accessory protein. The T cell is contacted in vivo or ex vivo. For example, a method of inducing an HIV-1 specific cytotoxic immune response in a subject such as a human is carried out by administering to the subject one or more of the HIV-1 polypeptides described herein. For prophylaxis, the polypeptide is administered to the subject prior to exposure of the subject to HIV-1 (i.e., the subject is uninfected with HIV). Alternatively, the polypeptide is administered to the subject after to exposure of the subject to HIV-1 to combat an ongoing infection. In some cases, the subject is a human adult (e.g., a pregnant woman); in other cases, the subject is a human infant (e.g. a newborn). The method optionally includes the step of diagnosing an HIV infection or an exposure to HIV. The immune responses elicted by the peptide epitopes (or nucleic acid constructs encoding them) are protective. For example, a previously-uninfected individual immunized with the compositions described herein does not develop clinical AIDS following exposure to HIV-1. In another example, the severity of disease on an HIV-infected individual is reduced following administration of the epitope peptides.

The peptides to be used in vaccines are at least 8 residues in length. For example, the peptides range in length from 10–500 amino acids. Peptides, which are 10, 20, 30, 40, or 50 amino acids in length are preferred. For example, the peptide is 9 to 15 amino acids in length.

Also within the invention are methods of identifying CTL epitopes in a target protein. The methods involve obtaining lymphocytes, e.g., peripheral blood mononuclear cells, from an HIV-1-infected individual and measuring the frequency of recognition of epitopes in HIV-1 infection. The methods preferably do not involve prior in vitro expansion of the patient-derived cells. Preferably, the methods include a step of non-specifically stimulating CD8+ T cells, e.g., using a bi-specific CD3/CD4 antibody. An increase in the frequency of recognition compared to other epitopes from the same target protein indicates that candidate epitope is dominant or is useful in a vaccine. The methods effectively and reliably identify epitopes within functionally active portions of the HIV-1 derived protein, thereby prioritizing peptides (e.g., immunodominant epitopes or conserved epitopes) to be used in vaccine production.

A vaccine, as used herein, is a preparation including materials that evoke a desired biological response, e.g., an immune response, in combination with a suitable carrier. The vaccine may include live organism, in which case it is usually administered orally, or killed organisms or components thereof, in which case it is usually administered parenterally. The cells used for the vaccine of the invention are preferably alive and thus capable of colonizing the intestines of the inoculated animal.

The polypeptides and nucleic acids encoding them are useful for vaccines or vaccine development. The polypeptides and nucleic acids are substantially pure. By a "substantially pure polypeptide" is meant a polypeptide which is separated from those components (proteins and other naturally-occurring organic molecules) which naturally accompany it. A polypeptide is substantially pure when it constitutes at least 60%, by weight, of the protein in the preparation. Preferably, the protein in the preparation is at least 75%, more preferably at least 90%, and most preferably at least 99%, by weight, of the desired peptide. A substantially pure polypeptide is obtained, e.g., by extraction from a natural source; by expression of a recombinant nucleic acid; or by chemically synthesizing the protein. Purity can be measured by any appropriate method, e.g., column chromatography, polyacrylamide gel electrophoresis, or HPLC analysis. A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include recombinant polypeptides derived from a eukaryote but produced in E. coli or another prokaryote, or in a eukaryote other than that from which the polypeptide was originally derived.

By "substantially pure DNA" is meant DNA that is free of the genes which, in the naturally-occurring genome of the organism from which the DNA of the invention is derived, flank the desired gene sequence. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Other embodiments and features of the invention will be apparent from the following description thereof, and from the claims.

BRIEF DESCRIPTION OF THE DRAWINGS

FIGS. 3A–J are histograms showing a determination of the HLA class I restriction of the novel CTL epitopes within HIV-1-Vif (peptide RIRTWKSLVK (SEQ ID NO:3)(RK10) and peptide HPRVSSEVHI (SEQ ID NO:4)(HI10)), using peptide-pulsed antigen presenting cells. The HLA class I type of the subject studied (AC-06) was A3/-, B7/-, Cw7/-. PBMC were incubated with either autologous antigen presenting cells (AC06-BCL) or antigen presenting cell lines only sharing one HLA class I allele with the subject studied (A3-, B7- and Cw7-Line). Antigen presenting cell lines were either incubated with the HI10 peptide or the RK10 peptide or with no peptide as negative controls (Nil). The percentage of IFN-γ producing CD8+ T cells are given in the individual plots.

FIGS. 4A–M are histograms showing a quantification of total HIV-1-specific CD8+ T cell activity at the single epitope level using intracellular IFN-g staining (ICS). HLA class I restriction, first and last amino residue, number of amino acids, protein and percentage of epitope-specific CD8+ T cells after subtraction of background activity are shown for each of the 12 CTL epitopes targeted by individual AC-06. Background activity in the negative control (NIL) was 0.09%.

FIG. 5D is a line graph showing that the isolated Vif-20-specific CD8+ T cells showed high cytotoxic activity in a standard $^{51}$chromium release assay against autologous BCL pulsed with the Vif-20 peptide or infected with recombinant vaccinia virus (rVV) expressing HIV-1 Vif . Background lysis of BCL pulsed with an non-HLA class I matched peptide (control) or infected with rVV-lac was below 5%, respectively.

DETAILED DESCRIPTION

Figure 1:
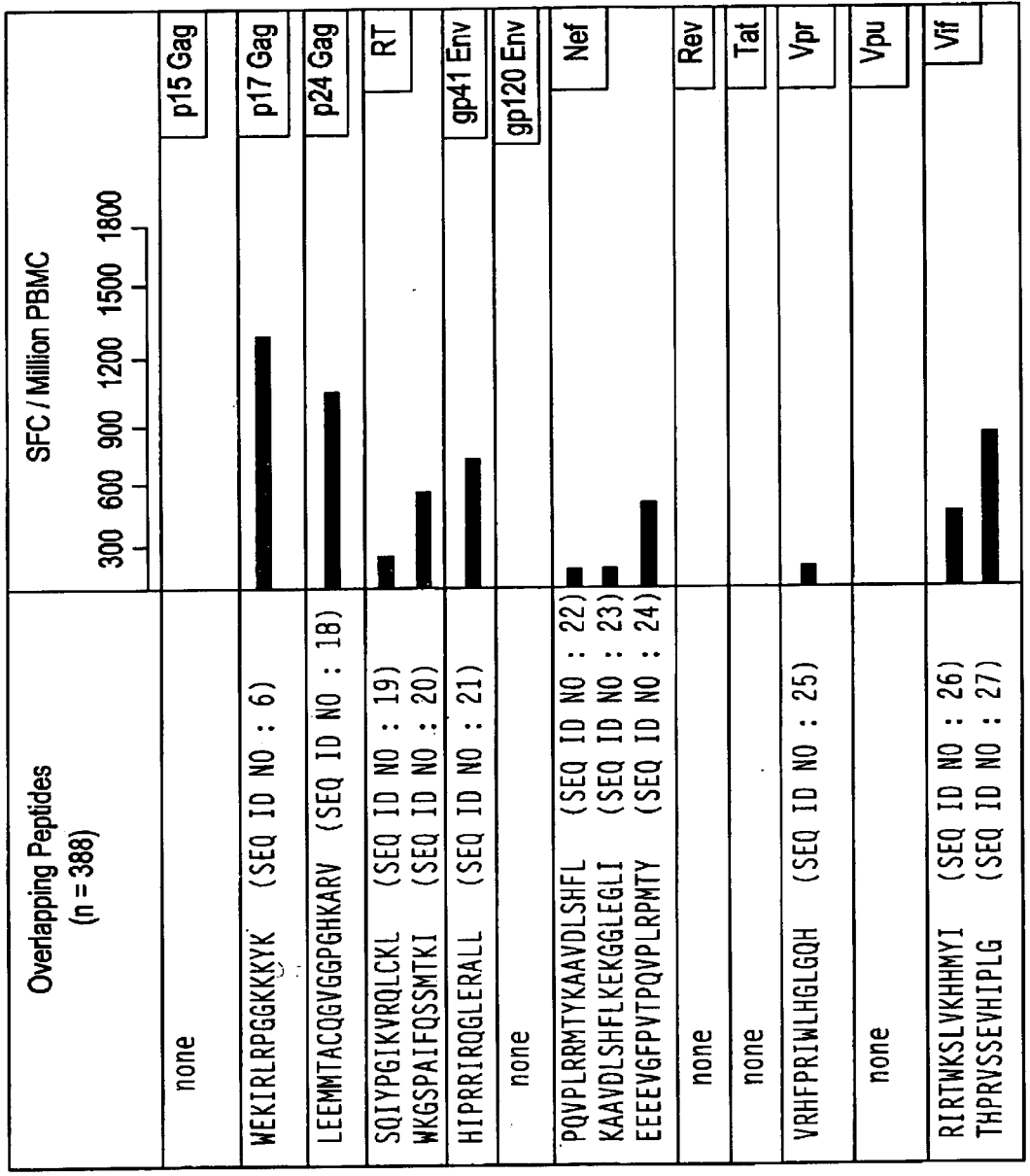
FIG. 1 is a bar graph showing HIV-1-specific CD8+ T cell responses determined by screening PBMC in an Elispot assay using overlapping peptides (15–20mer) spanning HIV-1 p15 (Gag), p17 (Gag), p24 (Gag), RT, gp41 (Env), gp120 (Env), Nef, Rev, Tat, Vpr, Vpu and Vif. The amino acid sequences of recognized peptides are shown and CD8+ T cell magnitudes are expressed as SFC/106 PBMC. A total of 4 different Vif peptides were recognized in this individual. However, these responses were induced by 2 epitopes contained within the overlap of each of two overlapping peptide pairs.

The relatively small accessory HIV-1 proteins Vpu, Vif and Vpr have important functions in viral disassembly, nuclear transport of the pre-integration complex, viral assembly and down-regulation of CD4 on the cell surface. These accessory proteins appear to be essential for viral replication.

HIV-1 Accessory Proteins

The accessory HIV-1 proteins Vpr, Vpu and Vif are essential for viral replication and have important roles in the early phases of the viral life cycle. HIV-1 Vpr is implicated in the nuclear translocation of the pre-integration complex after infection and the arrest of the cell cycle in the G2 phase. HIV-1 Vif may play an important role in viral disassembly after infection, the transport of incoming viral pre-integration complex (PIC) to the nucleus and HIV-1 provirus formation. Different structural regions within these proteins have been linked with their function. The Vpr protein contains four structural regions: the N-terminal region, the arginine-rich C-terminal region and one central domain containing two alpha helices (H$\alpha$1 and H$\alpha$2). The C-terminal basic region appears to be critical for the cell cycle arrest and that the two $\alpha$-helices are involved in the nuclear localization of the protein as well as the incorporation of Vpr into virus particle. The association between function and structure is less well established for HIV-1 Vif.

Cytoplasmic production of these accessory proteins suggests that they are processed for recognition by cytotoxic T lymphocytes. CTL responses against HIV-1 Vpr, Vpu and Vif were analyzed in 60 HIV-1 infected individuals and 10 HIV-1 negative controls using overlapping peptides spanning the entire proteins. Peptide-specific IFN-$\gamma$ production was measured by Elispot assay and flow-based intracellular cytokine quantification. HLA class I restriction and cytotoxic activity were confirmed after isolation of peptide-specific CD8+ T cell lines. CD8+ T cell responses against Vpr, Vpu and Vif were found in up to 45%, 2% and 33% of HIV-1 infected individuals, respectively. Multiple CTL epitopes were identified in functionally important regions of HIV-1 Vpr and Vif. Moreover, in infected individuals in whom the breadth of HIV-1-specific responses was assessed comprehensively, Vpr and p17 were the most preferentially targeted proteins per unit length by CD8+ T cells. These data indicate that despite the small size of these proteins Vif and Vpr are frequently targeted by CTL in natural HIV-1 infection and contribute importantly to the total HIV-1-specific CD8+ T cell responses. These findings are useful to evaluate the specificity and breadth of immune responses during acute and chronic infection, and in the design and testing of candidate HIV vaccines.

Therapeutic Administration

Peptides (or nucleic acids encoding the peptides) described herein are useful to induce HIV-specific CTL. The invention encompasses pharmaceutical, e.g., therapeutic, compositions. When a peptide is used as a vaccine or therapeutic agent, it is administered to a patient in the form of a peptide solution in a pharmaceutically acceptable carrier. Standard methods for intracellular delivery of peptides can be used, e.g. packaged in liposomes. Such methods are well known to those of ordinary skill in the art. It is expected that an intravenous dosage of approximately 1 to 100 $\mu$moles of the polypeptide of the invention would be administered per kg of body weight per day. The compositions of the invention are useful for parenteral administration, such as intravenous, subcutaneous, intramuscular, and intraperitoneal. For example, a unit dose of the peptide ranges from 0.1 to 100 mg, which may be administered, one time or repeatedly, to a patient. An accessory HIV peptide is administered alone or a plurality of selected epitope peptides are administered together (simultaneously or sequenctially). The accessory peptides are also co-administered with other HIV peptides such as Gag peptides.

Peptides are recombinantly produced or synthetically made using known methods. Peptide solutions are optionally lyophilized or granulated with a vehicle such as sugar. When the compositions are administered by injection, they are dissolved in distilled water or another pharmaceutically acceptable excipient prior to the injection. The peptides are mixed with an agents which enhance the immunogenicity of the peptides; such agents include BCG bacterial cells, ISCOM (Immunostimulating complex), QS-21, aluminum hydroxide (alum), and KLH (Keyhole Limpet Hemocyanin).

The peptides are used to induce anti-HIV CTL activity in vivo or ex vivo. The peptides are administered directly to an individual or lymphocytes (e.g., derived from peripheral blood mononuclear cells) are removed from an individual, cultured with one or more peptides, and returned to the individual. For example, 0.01 to 1 mg of the peptide is added to $10^7$ to $10^9$ peripheral blood lymphocytes originated from a patient, then the cells are cultivated for several hours to one day and thereafter they are intravenously administered to the patient. Alternatively, the cells are continuously cultivated in vitro in a culture medium to which recombinant interleukin 2 and 1 $\mu$g/ml of the peptide has been added. The cells are cultured over several weeks to induce CTL. Activated CTL are then intravenously injected into the patient.

DNA encoding a peptide epitope is incorporated into a viral vector for intracellular expression. The DNA is administered in a pharmaceutically acceptable carrier. The therapeutic composition may also include a gene delivery system such as a viral vector system. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a treated animal. As is well known in the medical arts, dosage for any given patient depends upon many factors, including the patient's size, body surface area, age, the particular compound to be administered, sex, time and route of administration, general health, and other drugs being administered concurrently. For example, nucleic acids are adminstered intravenously at a dose of approximately $10^6$ to $10^{22}$ copies of the nucleic acid molecule. Determination of optimal dosage is well within the abilities of a pharmacologist of ordinary skill.

Characterization of CTL Responses to HIV-1 Accessory Proteins

A detailed characterization of CTL responses to Vpu, Vif and Vpr was carried out using the materials and methods described below. The data provide evidence that the Vpr and Vif proteins represent important targets of cellular host defenses, whereas Vpu is infrequently recognized. In addition, the Vpr protein is one of the most frequently targeted HIV-1 proteins by CTL relative to the length of the protein. The data also provides a characterization of discrete CTL epitopes within these proteins, identified using overlapping peptides spanning the entire HIV-1 Vpr, Vpu and Vif sequence.

Subjects

Sixty HIV-1-infected and 10 HIV-1-negative individuals were studied. HIV-1-infected individuals included 45 subjects who were treated with highly active antiretroviral therapy (HAART) within 180 days of HIV-1 infection, 9 individuals with chronic treated HIV-1 infection and 6 individuals with long-term non-progressive HIV-1 infection, defined as viremia below 1000 HIV-1 RNA copies per ml for more than 6 years in the absence of any antiretroviral treatment. At the time of the CTL analysis, subjects on HAART had been effectively treated for at least 6 months and all had viral loads below 50 copies RNA/ml.

HLA-Typing

HLA class I molecular typing was performed using standard methods such as SSP-PCR (Bunce et al., 1995, Tissue Antigens 45:81).

Synthetic HIV-1 peptides

Peptides were synthesized on an automated peptide synthesizer (MBS 396, Advanced Chemtech, Louisville, Ky.) using standard methods such as Fmoc chemistry. Seventeen overlapping peptides spanning the HIV-1 SF2 B clade Vpr sequence, 14 overlapping peptides spanning the HIV-1 SF2 B clade Vpu sequence and 36 overlapping peptides spanning the HIV-1 SF2 B clade Vif sequence (12–18mers with 10 amino acid overlap) were generated. In addition, peptides corresponding to described optimal HIV-1 CTL epitopes (7) and a panel of 321 overlapping peptides (15–20mers) spanning the entire p15 Gag, p17 Gag, p24 Gag, gp41 Env, gp120 Env, RT, Rev, Tat and Nef sequence, were used.

Cell Lines and Media

EBV-transformed B lymphoblastoid cell lines (B-LCL) were established and maintained in R20 medium (RPMI 1640 medium (Sigma, St. Louis, Mo.) supplemented with 2 mM L-glutamine, 50 U/ml penicillin, 50 µg/ml streptomycin, 10 mM HEPES and 20% heat-inactivated FCS (Sigma)). For culture of CTL clones, medium containing 10% FCS (R10) supplemented with 50 U/ml recombinant interleukin-2.

Generation of Peptide-specific CD8+ T Cell Lines

CD8+ T cells were non-specifically expanded from PBMC over 10 days, using a bi-specific CD3/CD4 antibody. Peptide-specific CD8+ T cell lines were subsequently isolated using a standard IFN-γ catching assay. After expansion 10–20×10$^6$ CD8+ T cells were incubated on 24-well-plates with 20 µM peptide and 1 ug/ml each of the mAbs anti-CD28 and anti-CD49d (Becton Dickinson) at 37° C., 5% $CO_2$, for 6–8 hour. Cell were subsequently labeled with a bi-specific CD45/IFN-γ catching antibody and incubated for 45 min at 37° C., 5% $CO_2$. After several washes, the IFN-γ producing cells were stained with a second IFN-γ-PE detection antibody and separated by anti-PE mAb labeled with magnetic beads (MACS, Miltenyi Biotech, Hamburg, Germany). The isolated cells were then expanded for 10 days using autologous irradiated feeders.

Generation of CTL Clones

CTL clones were isolated by limiting dilution, using the anti-CD3-specific mAb 12F6 as stimulus for T cell proliferation. Developing clones were screened for HIV-1-specific CTL activity by $^{51}$chromium-release assay against autologous B-cell lines pulsed with the peptides recognized in the Elispot assays or infected with recombinant vaccina virus (rVV) expressing either HIV-1 Vpr or Vif. HIV-1-specific clones were maintained by stimulation every 14 to 21 days with an anti-CD3 monoclonal antibody and irradiated allogeneic PBMC. HLA-restriction of CTL epitopes was determined using a panel of target cells matched through only one of the HLA-A, HLA-B or HLA-C class I alleles expressed by the effector cells.

Elispot Assay

PBMC were plated on 96-well polyvinylidene difluoride-backed plates (MAIP S45, Millipore, Bedford, Mass.) that had been previously coated with 100 µl of an anti-IFN-γ mAB 1-D1k (0.5 µg/ml, Mabtech, Stockholm, Sweden) overnight at 4° C. Peptides were added directly to the wells at a final concentration of 1×10$^{-5}$ molar. Cells were added to the wells at 50,000 to 100,000 cells per well. The plates were incubated at 37° C., 5% $CO_2$ overnight (14–16 h) and then processed as described. IFN-γ producing cells were counted by direct visualization and are expressed as spot forming cells (SFC) per 10$^6$ cells. The number of specific IFN-γ secreting T-cells was calculated by subtracting the negative control value from the established SFC count. The negative controls were always <20 SFC per 10$^6$ input cells. Responses ≧40 SFC per 10$^6$ input cells above background were considered positive. The positive control consisted of incubation of 100,000 PBMC with phytohaemagglutinin (PHA). CD8+ T cell dependence of all responses to synthetic peptides was confirmed by loss of IFN-γ production after CD8+ T cell depletion using magnetic beads (MACS, Miltenyi Biotech, Germany), according to the manufacturer's protocol. Fine mapping of epitopes by Elispot assay was performed, using peptide truncations (e.g., as described in Altfield et al., 2000, J. Virol. 74:8541). 100,000 PBMC per well were incubated with concentrations from 10$^{-4}$ M to 10$^{-11}$ M of peptide overnight on the Elispot plate. All assays were run in duplicate. The optimal peptide was defined as the peptide that induced 50% maximal specific IFN-γ production of T-cells at the lowest peptide concentration.

Flow Cytometric Detection of Antigen-induced Intracellular IFN-γ

Intracellular cytokine staining assays were performed using known methods, e.g.,described by Pitcher et al., 1999, Nature Medicine 5:518 or Goulder et al, 2000, J. Exp. Med. 192:1819). 0.5–1.0 million PBMC were incubated on 24-well-plates with 2 µM peptide and 1 µg/ml each of the mAbs anti-CD28 and anti-CD49d (Becton Dickinson) at 37° C., 5% $CO_2$, for 1 hour, before the addition of 10 µg/ml Brefeldin A (Sigma, St Louis, Mo.). Following a further 5 hour incubation at 37° C., 5% $CO_2$, the cells were placed at 4° C. overnight. PBMC were then washed with PBS/1% BSA and stained with surface antibodies, anti-CD8 and anti-CD4 (Becton Dickinson) at 4° C. for 20 minutes. Following 3 further washes, the PBMC were fixed and permeabilized using Caltag Fixation/Permeabilization Kit (Caltag, Burlinghame, Calif.) and anti-IFN-γ-mAb (Becton Dickinson) was added. Cells were then washed and analyzed on a FACSort Flowcytometer (Becton Dickinson Immunocytometry systems, San Jose, Calif.) using peridinin chlorophyl protein (PerCP), allophycocyanin (APC) and fluorescein isothiocyanate (FITC) as fluorescent parameters. Control conditions were established by the use of autologous PBMC, which had not been stimulated with peptide, but otherwise had been treated identically. Cell population boundaries were established by exclusion of 99.97% of control lymphocytes. For the determination of HLA class I restriction of responses by flow cytometry, assays using HLA-matched or mismatched BCL were run (Goulder et al., 2001, J. Virol. 75:1339). BCL that were pulsed with 10 µM peptide for 1 hour were washed five times prior to incubation with effectors (10$^5$ BCL and 5×10$^5$ effectors) in 1 ml of R10. The mAbs anti-CD28 and anti-CD49d were then added and the assay run as described above.

Recognition of Vpr, Vpu and Vif Proteins by CD8+ T Cells from HIV-1 Infected Persons In order to determine whether the Vif, Vpr and/or Vpu proteins are targeted by the CTL response in HIV-1 infection, a study was carried out on individual AC-06. This individual had previously demonstrated responses to a total of nine CTL epitopes in p17, p24, RT, gp41 and Nef.

Optimal epitopes recognized within those gene products were determined. PBMC from subject AC-06 were analyzed by Elispot assay with a set of 388 overlapping peptides spanning the expressed HIV-1 clade B sequence. This allowed us to assess the relative contribution of Vpr-, Vpu- and Vif-specific CD8+ T cell responses to the overall CD8-mediated immune response. FIG. 1 shows the comprehensive characterization of HIV-1-specific CTL responses in this person using the entire panel of overlapping peptides including 17 peptides spanning Vpr, 14 peptides spanning Vpu and 36 peptides spanning Vif, as well as peptides spanning p15, p17, p24, RT, gp41, gp120, Nef, Rev and Tat. CD8+ T cell dependence of all responses was confirmed by CD8/CD4 depletion studies. In addition to the nine previously demonstrated CTL responses, at least 2 responses to Vif and one to Vpr were detected (FIG. 1). Of all of the responses detected, the response to an epitope contained in the Vif peptide THPRVSSEVHIPLG (SEQ ID NO:5) was the third highest in magnitude (1180 SFC/$10^6$ PBMC). These data indicate that multiple accessory proteins can be targeted simultaneously by the CTL response in a single individual, and failure to assess these responses would lead to an underestimation of responses.

Definition of Optimal CTL Epitopes within the Accessory HIV-1 Proteins

Figure 2A:
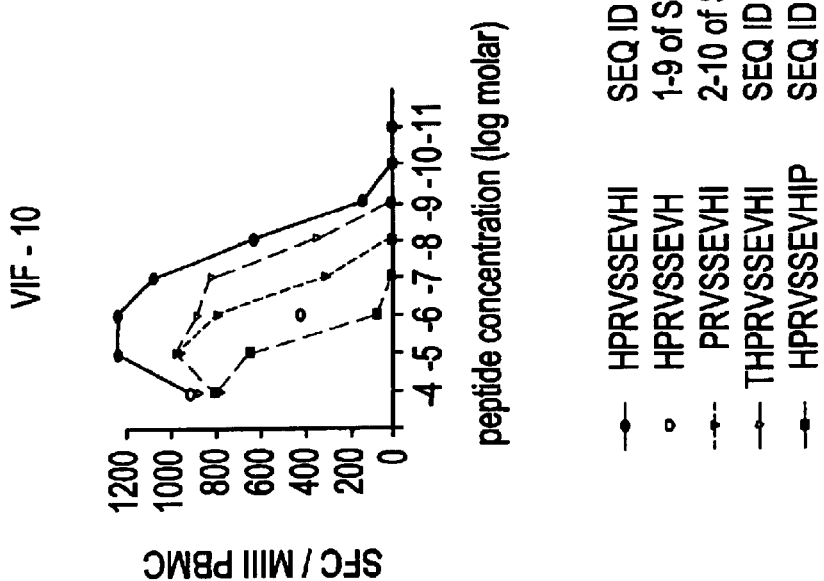
FIGS. 2A–B are line graphs showing a definition of two novel optimal CTL epitopes within HIV-1 Vif. Titration curves using PBMC in an Elispot assay incubated with serial dilutions of truncated peptides within the Vif-3 peptide (FIG. 2A) and Vif-10 peptide (FIG. 2B). The truncated peptides used are shown and the optimal CTL epitope was defined as the peptide inducing 50% of maximal specific IFN-γ production of T cells at the lowest peptide concentration (RIRTWKSLVK (SEQ ID NO:3 for Vif-3 and HPRVSSEVHI (SEQ ID NO:4)for Vif-10).
Figure 2B:
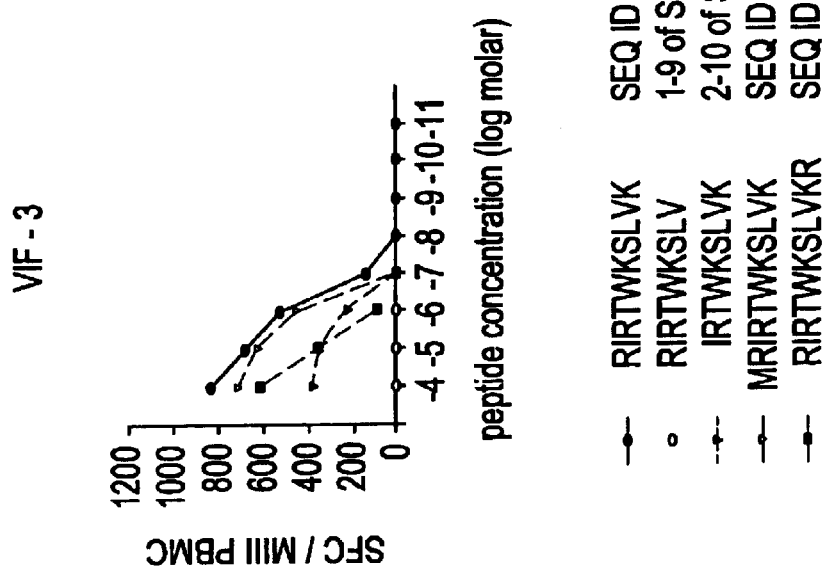
Figures 4A, 4B, 4C, 4D, 4E, 4F:
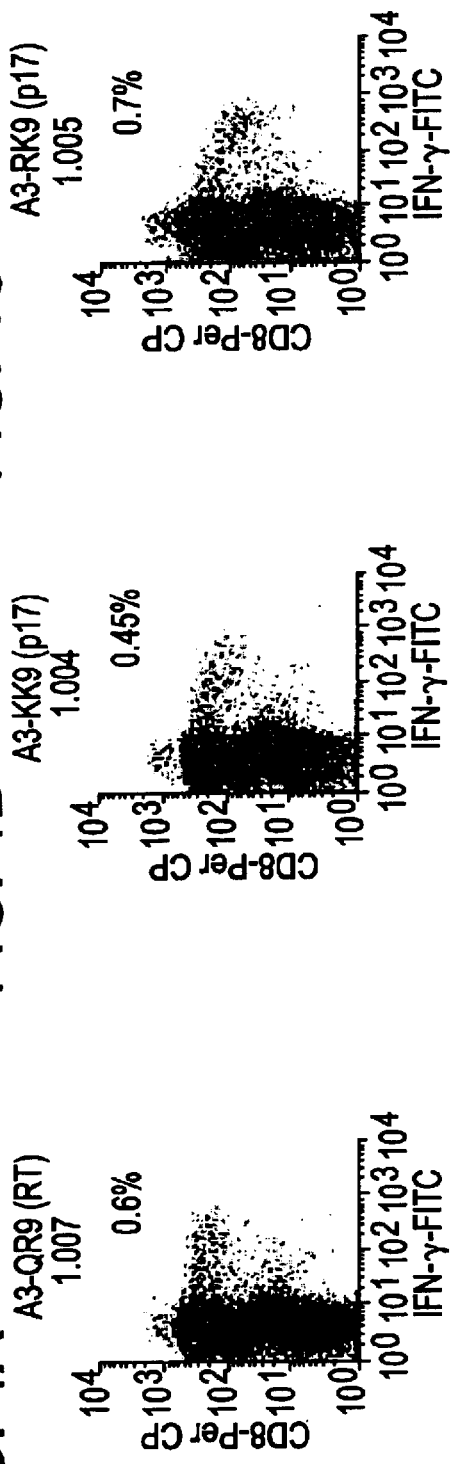

The data indicated that Vif and Vpr were targeted by CD8 cells in this individual, but do not indicate the number of epitopes contained within each of the proteins. For example, the p17 Gag peptide WEKIRLRPGGKKKYK (SEQ ID NO:6) actually contains two discrete A3-restricted epitopes, KIRLRPGGK (residues 3–11 of SEQ ID NO:6) and RLRPGGKKK (residues 7–13 of SEQ ID NO:6), and responses to two peptides in Vif that share a 10 amino acid overlap could represent targeting of an epitope shared by both peptides, or two discrete epitopes. In order to determine the contribution of epitopes within the accessory proteins to the overall breadth of the CTL response in this person, the optimal epitopes within these longer peptides were determined. This is exemplified for the two CTL epitopes within HIV-1 Vif (FIGS. 2A–B and FIGS. 3A–J). The optimal sequences of these novel CTL epitopes were determined by Elispot assay, using PBMC and serial dilutions of truncated peptides (FIGS. 2A–B). The peptide that induced specific IFN-γ-production at the lowest peptide concentration was defined as the optimal CTL epitope (FIG. 2A: RIRTWKSLVK (SEQ ID NO:3) (RK10) for Vif-3; FIG. 2B: HPRVSSEVHI (SEQ ID NO:4) (HI10) for Vif-10). The HLA-restriction of these CTL epitopes was subsequently determined by flow cytometric quantification of peptide-specific IFN-γ production using PBMC and partially HLA class I matched antigen presenting cells (APC) (FIGS. 3A–J). The Vif-RK10 peptide induced IFN-γ production of CD8+ T cells only when presented by autologous APC or APC expressing HLA-A3, demonstrating that this epitope was restricted by HLA-A3. This peptide also conforms precisely to the predicted motif for HLA-A3-presented peptides, with a non-polar residue in position 2 and a lysine at the C-terminal of the peptide. In contrast, the Vif-HI10 peptide was restricted by HLA-B7 (FIGS. 3A–J), and conformed to the predicted motif for this allele. The sequence of the optimal CTL epitope as well as the HLA class I restriction was subsequently reconfirmed using a standard $^{51}$chromium release assay following the isolation of peptide-specific CTL clones by limiting dilution. In all, three novel CTL epitopes in two accessory HIV-1 proteins were identified by the use of overlapping peptides in this single patient (Table I). Of the total of 12 epitopes targeted by individual AC-06, 3 (25%) were located in the accessory proteins Vif and Vpr.

TABLE I

Novel optimal CTL epitopes in individual AC-06

| HIV-1 protein | aa-position | sequence | HLA-restriction |
| --- | --- | --- | --- |
| Vif | 17–26 | RIRTWKSLVK (SEQ ID NO:3) | A*0301 |
| Vif | 48–57 | HPRVSSEVHI (SEQ ID NO:4) | B*0702 |
| Vpr | 34–42 | FPRIWLHGL (SEQ ID NO:9) | B*0702 |

The contribution of responses directed against the individual CTL epitopes contained within the overlapping peptides to the total HIV-1-specific CTL responses in subject AC-06 was determined using intracellular IFN-γ quantification by flow cytometry (FIGS. 4A–M). Inter-assay variation, defined as the standard deviation divided by the mean of the responses between assays run multiple times in parallel, was less than 12%, as determined in previous experiments to evaluate this technique. Of the CD8+ T cells, 15.6% were specific for the tested HIV-1 CTL epitopes. The immunodominant response in this subject was directed against the HLA-B7-restricted CTL epitope GPGHKARVL (SEQ ID NO:7) (GL9) in p24 Gag. A total of 5.6% of CD8+ T cells were directed against this epitope, contributing 32% to the total HIV-1-specific CD8 responses. CD8+ T cell responses directed against the accessory proteins Vif and Vpr contributed importantly to the total responses (17% of total HIV-1-specific CD8 responses) in this subject. These data therefore indicate that the breadth and magnitude of the CTL responses in this person would have been underestimated by 25% and 17%, respectively, had responses directed against the accessory HIV-1 proteins Vif, Vpr and Vpu not been assessed.

Frequency of Recognition of the HIV-1 Proteins Vif, Vpr and Vpu in HIV-1 Infection The data described above indicate that CD8+ T cell responses can target epitopes within the accessory HIV-1 proteins Vif, Vpr and Vpu. In order to characterize CD8+ T cell responses directed against these accessory proteins in more detail, 60 HIV-1 infected individuals at different stages of infection (45 individuals with treated acute HIV-1 infection, 9 individuals with treated chronic infection and 6 individuals with long-term non-progressive infection) were screened for CD8+ T cell responses against these proteins by using overlapping peptides in an IFN-γ Elispot assay. PBMC from 27/60 (45%) HIV-1-positive study subjects recognized at least 1 overlapping Vpr peptide (Table II), 20/60 (33%) individuals had responses against 1 or more Vif peptides (Table III) and only one individual had responses against the Vpu peptides (individual CMW with long-term non-progressive HIV-1 infection had confirmed responses against the Vpu-6 peptides at 170 SFC/Mill PBMC). Magnitude of responses against the Vpr peptides ranged from 40–1400 SFC/Mill PBMC (median 245), with Vpr-12 being the most frequently targeted. Responses against the Vif peptides range from 40–1100 SFC/Mill PBMC (median 215), with Vif-6 being the most frequently targeted. CD4-depletion assays and flow-based analysis of peptide-specific intracellular IFN-γ production determined that all responses against the accessory proteins were CD8+ T cell mediated. Individuals with long-term non-progressive and treated chronic HIV-1 infection targeted the Vpr more frequently than individuals with treated acute infection (p=0.03, twotailed Fischer's Exact Test), but not Vif (p=0.8). This observation for HIV-1 Vpr is in line with the observation that individuals treated during acute HIV-1 infection have a narrowly directed CTL response, compared to individuals treated later in the course of infection. Responses against the tested Vif, Vpr and Vpu peptides were <20 SFC/Mill PBMC (range 0–20 SFC/Mill PBMC, median 0 SFC/Mill PBMC) in the 10 HIV-1-negative individuals used as controls.

TABLE II

Magnitude of peptide-specific CD8+ T cell responses directed against Vpr overlapping peptides as measured by IFN-γ ELISPOT (SFC/10⁶ PBMC)

|  | vpr-2 | vpr-3 | vpr-4 | vpr-6 | vpr-7 | vpr-9 | vpr-10 | vpr-11 | vpr-12 | vpr-13 |
|---|---|---|---|---|---|---|---|---|---|---|
| AC-43 | 0 | 0 | 0 | 80 | 0 | 0 | 0 | 0 | 0 | 0 |
| AC-10 | 0 | 0 | 0 | 0 | 0 | 600 | 0 | 0 | 0 | 0 |
| AC-46 | 0 | 0 | 0 | 0 | 0 | 0 | 0 | 0 | 850 | 0 |
| AC-49 | 0 | 0 | 0 | 0 | 110 | 0 | 0 | 0 | 0 | 0 |
| AC-31 | 0 | 0 | 0 | 0 | 0 | 0 | 0 | 0 | 0 | 0 |
| CMW | 0 | 0 | 0 | 0 | 0 | 40 | 0 | 0 | 0 | 0 |
| AC-04 | 0 | 0 | 0 | 0 | 0 | 0 | 0 | 0 | 450 | 0 |
| AC-27 | 0 | 0 | 0 | 310 | 0 | 0 | 0 | 0 | 0 | 0 |
| AC-59 | 0 | 0 | 0 | 0 | 380 | 0 | 0 | 0 | 0 | 0 |
| AC-38 | 0 | 0 | 0 | 0 | 210 | 0 | 0 | 0 | 0 | 0 |
| AC-09 | 280 | 260 | 0 | 0 | 0 | 0 | 0 | 0 | 310 | 0 |
| AC-13 | 0 | 0 | 0 | 130 | 0 | 0 | 0 | 0 | 220 | 0 |
| JMV | 0 | 0 | 0 | 0 | 150 | 0 | 0 | 0 | 0 | 0 |
| JRH | 0 | 0 | 0 | 0 | 0 | 0 | 0 | 0 | 1400 | 0 |
| AC-06 | 0 | 0 | 0 | 0 | 250 | 0 | 0 | 0 | 0 | 0 |
| AC-60 | 0 | 0 | 0 | 0 | 0 | 1300 | 1200 | 0 | 360 | 0 |
| 6002 | 0 | 0 | 0 | 0 | 0 | 0 | 0 | 0 | 50 | 0 |
| 6005 | 0 | 0 | 0 | 0 | 0 | 0 | 0 | 0 | 70 | 0 |
| 6003 | 0 | 0 | 0 | 60 | 0 | 0 | 0 | 0 | 0 | 0 |
| 6009 | 0 | 0 | 0 | 0 | 0 | 40 | 0 | 0 | 0 | 0 |
| 6010 | 0 | 0 | 0 | 0 | 0 | 0 | 0 | 130 | 0 | 0 |
| MJR | 0 | 0 | 0 | 0 | 170 | 370 | 0 | 180 | 180 | 0 |
| TMH#4 | 0 | 0 | 340 | 250 | 240 | 220 | 0 | 0 | 0 | 0 |
| TMH#6 | 0 | 0 | 0 | 0 | 0 | 0 | 0 | 0 | 250 | 0 |
| CWE | 0 | 0 | 0 | 0 | 0 | 0 | 0 | 0 | 540 | 380 |
| AC-TZA | 0 | 0 | 0 | 260 | 0 | 0 | 0 | 0 | 0 | 0 |
| AC-55 | 80 | 0 | 0 | 0 | 0 | 0 | 0 | 0 | 0 | 0 |

TABLE III

Magnitude of peptide-specific CD8+ T cell responses directed against Vif overlapping peptides as measured by IFN-γ ELISPOT (SFC/10⁶ PMBC)

|  | vif-2 | vif-3 | vif-4 | vif-6 | vif-7 | vif-8 | vif-9 | vif-10 | vif-12 | vif-13 | vif-14 | vif-15 | vif-16 | vif-18 |
|---|---|---|---|---|---|---|---|---|---|---|---|---|---|---|
| AC-43 | 0 | 0 | 0 | 220 | 0 | 0 | 0 | 0 | 0 | 0 | 0 | 0 | 0 | 0 |
| AC-46 | 0 | 0 | 0 | 230 | 0 | 0 | 0 | 0 | 0 | 0 | 0 | 0 | 0 | 0 |
| AC-31 | 0 | 0 | 0 | 0 | 0 | 0 | 0 | 0 | 160 | 240 | 0 | 0 | 0 | 0 |
| CMW | 0 | 0 | 0 | 0 | 0 | 0 | 0 | 0 | 0 | 0 | 0 | 0 | 150 | 0 |
| AC-04 | 0 | 0 | 0 | 0 | 0 | 0 | 0 | 0 | 0 | 0 | 0 | 0 | 0 | 130 |
| AC-42 | 0 | 0 | 0 | 0 | 0 | 0 | 0 | 0 | 0 | 0 | 0 | 0 | 0 | 0 |
| AC-27 | 0 | 0 | 0 | 350 | 0 | 0 | 0 | 0 | 0 | 0 | 0 | 0 | 0 | 0 |
| AC-59 | 0 | 0 | 0 | 1100 | 170 | 0 | 280 | 840 | 0 | 0 | 0 | 0 | 0 | 0 |
| AC-01 | 0 | 0 | 0 | 0 | 0 | 0 | 0 | 0 | 60 | 60 | 0 | 0 | 0 | 0 |
| AC-13 | 0 | 0 | 0 | 0 | 0 | 0 | 0 | 0 | 0 | 0 | 0 | 0 | 0 | 0 |
| JMV | 0 | 0 | 0 | 0 | 0 | 0 | 0 | 0 | 270 | 310 | 0 | 0 | 0 | 0 |
| JRH | 490 | 430 | 0 | 0 | 0 | 0 | 0 | 0 | 0 | 0 | 0 | 0 | 0 | 0 |
| AC-06 | 0 | 680 | 620 | 0 | 0 | 0 | 850 | 11800 | 0 | 0 | 0 | 0 | 0 | 0 |
| AC-07 | 0 | 0 | 0 | 0 | 90 | 0 | 0 | 0 | 0 | 0 | 0 | 0 | 0 | 0 |
| 6003 | 0 | 0 | 0 | 40 | 0 | 0 | 0 | 0 | 0 | 0 | 0 | 0 | 0 | 0 |
| 6009 | 50 | 290 | 170 | 0 | 0 | 50 | 40 | 40 | 0 | 0 | 0 | 0 | 0 | 0 |
| 6007 | 0 | 0 | 0 | 0 | 260 | 210 | 0 | 0 | 0 | 0 | 0 | 0 | 0 | 0 |
| TMH#4 | 0 | 0 | 0 | 0 | 0 | 0 | 0 | 0 | 0 | 0 | 0 | 0 | 80 | 0 |
| AC-TZA | 0 | 0 | 0 | 0 | 0 | 0 | 0 | 0 | 0 | 0 | 240 | 110 | 0 | 0 |
| AC-36 | 0 | 0 | 0 | 0 | 0 | 0 | 0 | 0 | 50 | 100 | 0 | 0 | 0 | 0 |

|  | vif-20 | vif-27 | vif-28 | vif-29 | vif-30 | vif-31 |
|---|---|---|---|---|---|---|
| AC-43 | 0 | 0 | 0 | 0 | 0 | 0 |
| AC-46 | 0 | 0 | 0 | 0 | 0 | 0 |
| AC-31 | 0 | 0 | 0 | 0 | 0 | 0 |
| CMW | 0 | 0 | 0 | 0 | 0 | 0 |
| AC-04 | 880 | 0 | 0 | 0 | 0 | 0 |
| AC-42 | 220 | 0 | 0 | 0 | 0 | 0 |
| AC-27 | 0 | 0 | 0 | 0 | 0 | 0 |

TABLE III-continued

Magnitude of peptide-specific CD8+ T cell responses directed against Vif overlapping peptides as measured by IFN-γ ELISPOT (SFC/10⁶ PMBC)

| | | | | | | |
|---|---|---|---|---|---|---|
| AC-59 | 0 | 0 | 0 | 0 | 0 | 0 |
| AC-01 | 0 | 0 | 0 | 0 | 0 | 0 |
| AC-13 | 0 | 0 | 260 | 0 | 0 | 0 |
| JMV | 0 | 50 | 0 | 90 | 0 | 0 |
| JRH | 0 | 0 | 0 | 0 | 0 | 0 |
| AC-06 | 0 | 0 | 0 | 0 | 190 | 390 |
| AC-07 | 0 | 0 | 0 | 0 | 0 | 0 |
| 6003 | 0 | 0 | 0 | 0 | 0 | 0 |
| 6009 | 0 | 0 | 0 | 0 | 0 | 0 |
| 6007 | 0 | 0 | 0 | 0 | 0 | 0 |
| TMH#4 | 0 | 0 | 0 | 0 | 0 | 0 |
| AC-TZA | 0 | 0 | 0 | 0 | 0 | 0 |
| AC-36 | 0 | 0 | 0 | 0 | 0 | 0 |

TABLE IV

| | Subjects with CTL responses against HIV-1 | | | | | | | | | | |
|---|---|---|---|---|---|---|---|---|---|---|---|
| | vpu | vpr | vif | tat | rev | p15 | p17 | p24 | gp41 | RT | nef |
| Responders (n = 29) | 0 | 15 (52%) | 10 (35%) | 5 (17%) | 8 (28%) | 14 (48%) | 22 (76%) | 21 (72%) | 8 (28%) | 16 (55%) | 20 (79%) |
| No. amino acids | 78 | 96 | 191 | 88 | 116 | 137 | 130 | 240 | 350 | 560 | 205 |
| Amino acid adjusted score* | 0 | 0.54 | 0.18 | 0.19 | 0.24 | 0.34 | 0.59 | 0.30 | 0.08 | 0.1 | 0.39 |

*Frequency of recognition in percentage divided by number of amino acids per protein Frequency of Recognition of Accessory Proteins Compared to Other HIV-1 Proteins Studies were carried out to determine how frequently the accessory proteins Vif, Vpr and Vpu were recognized compared to other HIV-1 proteins. A subset of 29 HIV-1-infected individuals (4 LTNP, 17 with acute treated and 8 with chronic treated infection) were screened with a panel of 388 overlapping peptides spanning the entire Gag, gp41, RT, Rev, Tat, Vpr, Vpu, Vif and Nef sequence, as described above for subject AC-06 (FIG. 1), and frequencies of recognition were compared (Table IV). Furthermore, the frequency of recognition was adjusted for the length of the proteins by dividing frequency by the number of amino acids per protein. Adjusted for its length, the HIV-1 Vpr and p17 Gag proteins were the most frequently targeted HIV-1 proteins in natural HIV-1 infection, while HIV-1 Vif was targeted as frequently as HIV-1 RT, gp41 or Tat. In order to exclude a potential bias towards an over-representation of responses directed against HIV-1 Vpr and p17 Gag due to the high frequency of individuals with HLA-A2 in the study cohort (40%) and the presence of epitopes restricted by this allele in both proteins (SLYNTVATL (SEQ ID NO:8) in p17 and AIIRLLQQL (SEQ ID NO:1) in Vpr), the analysis was repeated after the exclusion of individuals expressing HLA-A2. HIV-1 Vpr and p17 Gag remained the most frequently targeted proteins within HIV-1, with length adapted scores of 0.44 and 0.61. Comparing the frequency of recognition of different HIV-1 proteins among individuals with acute treated, chronic treated and long-term non-progressive HIV-1 infection, LTNP and individuals with chronic treated infection had CD8+ T cell responses directed against more epitopes and more HIV-1 proteins as for the structural HIV-1 proteins, but these differences did not reach statistical significance (Fisher exact test, p>0.1). Taken together, these data extend the studies in AC-06 to show that the accessory proteins are frequently targeted by CD8+ T cells in HIV-1 infection.

Identification of Additional CTL Epitopes within the Accessory HIV-1 Proteins

Figure 5G:
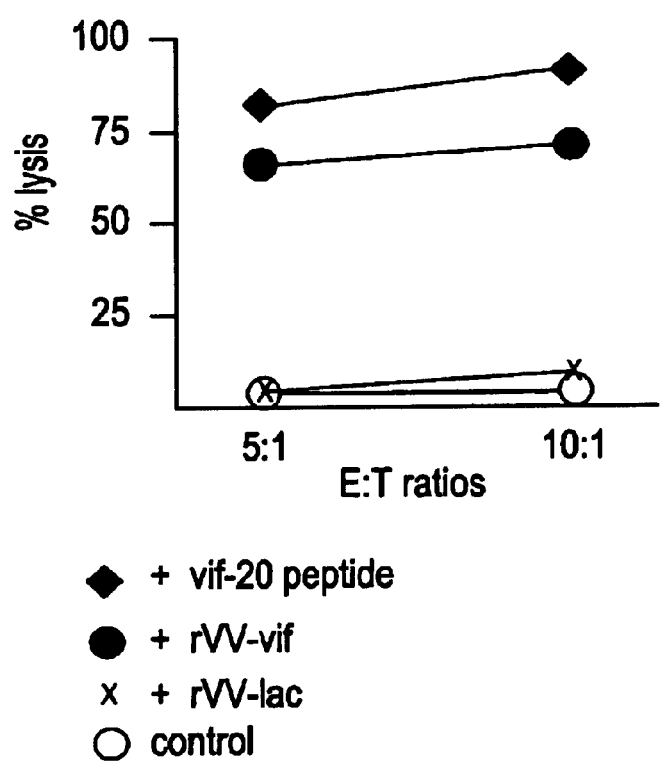
FIGS. 5A–F are histograms showing an isolation of peptide-specific CD8+ T cell lines specific for peptide Vif-20. The percentage of CD8+ T cells specific for the Vif-20 peptide in individual AC04 was quantified using PBMC (FIG. 5AB), CD8+ T cell lines after 10 days non-specific expansion with a CD3/CD4 bi-specific mAB (FIGS. 5C–F) and following the isolation and expansion of antigen-specific CD8+ T cells using the IFN-g catching assay.

Despite over 140 optimal CTL epitopes defined to date, no Vif and Vpu epitopes have been mapped and only 2 HLA-A2-restricted epitopes within Vpr, predicted by the HLA-A2 peptide-binding motif, have been described. In addition to the 3 novel HLA-A3- and B7-restricted CTL epitopes described above in subject AC-06, the optimal CTL epitopes restricted by different HLA class I molecules were characterized for peptides recognized frequently in the studied individuals and determined the percentage of individuals with the corresponding HLA-type recognizing the epitope (Table V). For all novel CTL epitopes the optimal peptide sequence was defined using serial dilutions of truncated peptides as described above and the HLA class I restriction was determined by using peptides presented by autologous and partially HLA-matched cell lines. Optimal CTL epitopes were defined by Elispot and flow-based assays using PBMC in most cases and reconfirmed after isolation of peptide-specific cytotoxic CD8+ T cell lines in a standard $^{51}$chromium release assay. For the HLA-B*1801- and HLA-B*5701-restricted CTL responses in Vif and the HLA-B*5701-restricted CTL response in Vpr, the frequency of peptide-specific CD8+ T cells in the peripheral blood was not sufficiently high to determine the optimal epitope sequence and the HLA-restriction of the response directly using PBMC. For the characterization of these epitopes, CD8+ T cells were non-specifically expanded using a CD4/CD3-bispecific antibody and peptide-specific CD8+ T cell lines were subsequently isolated using a newly adapted IFN-γ catching assay that allows for the isolation of peptide-activated CD8+ T cells using magnetic beads. This is shown for the CD8+ T cells specific to the Vif-20 peptide in individual AC-04 (FIGS. 5A–F). 0.3% of fresh PBMC targeted this peptide (FIG. 5a). After a 10-day expansion of CD8+ T cells using a bi-specific CD3/CD4 antibody and IL-2, the peptide-specific CD8 population was expanded to 1.3% (FIGS. 5A–F). The frequency of these Vif-20-specific CD8+ T cells was further increased to 67% after isolation of peptide-specific cells using the IFN-γ catching assay (FIGS. 4A–M). CD8+ T cell lines isolated this way showed strong (>80%) peptide-specific cytotoxic activity at different effector to target ratios in a standard $^{51}$chromium release assay (FIGS. 4A–M) and were used to determine the HLA class I restriction and minimal sequence of these novel epitopes by standard cytotoxicity assays. These peptide-specific lines were also used in a cytotoxicity assay with autologous B-lymphoblastoid cells infected with rVV expressing Vpr and Vif to demonstrate that the novel epitopes defined were effectively processed intracellularly, as shown for the HLA-B*1801-restricted CTL response in Vif(FIGS. 5A–F).

Taken together, a total of 9 novel CTL epitopes within the accessory HIV-1 proteins were identified and characterized. Several of these novel epitopes were restricted by HLA class I alleles common in the studied cohort, including HLA-A*0201, -A*0301 and -B*0702 (Table V). The most frequently recognized CTL epitopes were the HLA-A*0201-restricted epitope AIIRILQQL (SEQ ID NO:1) (AL9) or ALIRILQQL (SEQ ID NO:2) and the HLA-B*0702-restricted epitope FPRIWLHGL (SEQ ID NO:9) (FL9) in Vpr. HIV-1 strains containing the sequence of SEQ ID NO:2 and peptide immunogens containing the sequence elicit a potent CTL response against HIV containing SEQ ID NO:2 as well as SEQ ID NO:1. The level of the immune response elicited by SEQ ID NO:2 is at least 1 log greater than that elicted by SEQ ID NO:1. These data indicate that peptides containing the amino acid sequence of SEQ ID NO:2 are more potent and superior immunogens (and thus, more valuable vaccine compositions) compared to those containing the amino acid sequence of SEQ ID NO:1).

AL9 was targeted by one third (6/18) of the individuals expressing the HLA-A2 allele. FL9 was recognized by 4/8 individuals expressing the HLA-B7, as well as by the two individuals in this cohort that expressed HLA-B*8101, an HLA class I allele common in African population, indicating a high degree of cross-presentation and -recognition between these closely related HLA class I alleles. Also, 2 novel epitopes restricted by HLA-B*5701, an allele associated with long-term non-progressive HIV-1 infection, were identified and frequently recognized in individuals expressing the corresponding allele (Table V). These studies not only characterize multiple epitopes within these accessory proteins, but show that the CD8+ T cell responses detected are associated not only with IFN-γ production but also with cytolysis.

TABLE V

Novel optimal CTL epitopes within HIV-1 Vpr and Vif and frequency of recognition

| HIV-1 protein | aa-position | sequence | HLA-restriction | recognition* |
|---|---|---|---|---|
| Vpr | 12–20 | REPHNEWTL (SEQ ID NO:10) | B*4002 | 1/1 |
| Vpr | 29–38 | AVRHFPRIW (SEQ ID NO:11) | B*5701 | 4/6 |
| Vpr | 34–42 | FPRIWLHGL (SEQ ID NO:9) | B*8101 | 2/2 |
| Vpr | 34–42 | FPRIWLHGL (SEQ ID NO:9) | B*0702 | 4/8 |
| Vpr | 58–66 | ALIRILQQL (SEQ ID NO:2) | A*0201 | 8/24 |
| Vif | 17–26 | RIRTWKSLVK (SEQ ID NO:3) | A*0301 | 3/15 |

TABLE V-continued

Novel optimal CTL epitopes within HIV-1 Vpr and Vif and frequency of recognition

| HIV-1 protein | aa-position | sequence | HLA-restriction | recognition* |
|---|---|---|---|---|
| Vif | 31–39 | ISKKAKGWF (SEQ ID NO:12) | B*5701 | 2/6 |
| Vif | 48–57 | HPRVSSEVHI (SEQ ID NO:4) | B*0702 | 3/8 |
| Vif | 102–111 | LADQLIHLHY (SEQ ID NO:13) | B*1801 | 2/5 |

*Individuals with the corresponding HLA class I alleles that responded to the epitope Identification and Characterization of Optimal CTL Epitopes Increasing evidence suggests that a comprehensive assessment of CD8+ T cell responses against HIV-1 is necessary in order to interpret the entire magnitude and breadth of these responses. The use of overlapping peptide spanning the HIV-1 structural as well as regulatory proteins allows for a detailed characterization of HIV-1-specific CTL responses and the identification of novel CTL epitopes within these proteins. However, the relative contribution of CTL responses directed against the accessory HIV-proteins Vpr, Vpu and Vif have not been studied prior to the invention. In these studies CD8+ T cell responses directed against these accessory proteins were characterized in 60 HIV-1 infected individuals comprehensively by using overlapping peptides spanning the entire Vpr, Vpu and Vif sequence of HIV-1. The data described herein demonstrate that the accessory HIV-1 proteins Vpr and Vif are frequently targeted by HIV-1-specific CD8+ T cells, with 45% and 33% of the tested individuals having detectable responses to these proteins, respectively, contributing importantly to the total HIV-1-specific CTL responses. In contrast, HIV-1 Vpu is rarely targeted by CTL in infected individuals. These studies also indicate that there are multiple epitopes contained within Vif and Vpr, and include fine mapping of several optimal CTL epitopes within these proteins.

In these studies, a comprehensive set spanning expressed HIV-proteins was used to characterize the relative role of each protein as a target for CD8+ T cell responses. HIV-1 Vpr was found to be the most frequently targeted HIV-1 protein, together with p17 Gag, when adapted to the amino acid length of the protein. Several factors may contribute to the high recognition of Vpr and p17 by virus-specific CTL. First, the high frequency of HLA-A2 in our Caucasian study population may have contributed to an over-representation of Vpr- and p17 (Gag)-specific responses due to immunodominat HLA-A2-restricted CTL epitopes within p17 and Vpr. However, a re-evaluation of the data after the exclusion of individuals expressing HLA-A2 from the analysis showed that the frequent recognition of HIV-1 Vpr was independent from the over-representation of this allele in the study cohort. Another factor influencing the recognition of viral proteins by CTL may be the amount of expression of these proteins during viral infection, with proteins expressed at high frequencies being more frequently targeted by CTL. Indeed, HIV-1 Gag and HIV-1 Vpr are expressed at higher levels in infected cells compared to HIV-1 Pol and also at higher levels compared to HIV-1 Vif. Finally, the degree of sequence conservation within a particular HIV-1 protein may influence its recognition by CTL, as these proteins are less likely to escape from CTL mediated immune pressure, leading to the potential accumulation of responses directed against these more conserved proteins. HIV-1 p17 and Vpr are relatively highly conserved, but are not more conserved than RT, which was much less frequently targeted. Taken together, these data indicate that responses directed against the accessory HIV-1 proteins are frequently detected in natural HIV-1 infection and may contribute importantly to the total virus-specific CD8+ T cell responses.

Methods of Identifying CTL Epitopes

Techniques were developed to allow a more rapid characterization of novel CTL epitopes, using PBMC with no prior in vitro expansion. These techniques include the fine-mapping of novel CTL epitopes using serial dilutions of truncated peptides in an Elispot assay and the determination of HLA restriction of these novel epitopes using antigen presenting cells only sharing one HLA class I allele with the corresponding donor in a flow-based restriction assay. These techniques require a frequency of CD8+ T cells specific for the studied epitope of at least 0.3%, in particular for the flow-based HLA restriction assay, in order to provide significant and reliable results.

Another technique that allows for the rapid generation of peptide-specific CD8+ T cell lines, including lines specific for epitopes recognized by CD8+ T cells at low frequencies. The non-specific stimulation of CD8+ T cells with a bi-specific CD3/CD4-antibody allows for the expansion of CD8+ T cells to levels that enable the sorting of peptide-specific CD8+ T cells in an IFN-γ catching assay using magnetic beads. These peptide-specific CD8+ T cells are further expanded after restimulation with autologous feeder cells and exhibit strong peptide-specific cytotoxic activity in a standard $^{51}$chromium release assay. This assay facilitates the identification of novel CTL epitopes and allows for the rapid generation of epitope-specific T cell lines that can subsequently be used for functional assays.

Several of the newly defined CTL epitopes map to important functional domains within the Vpr protein. The most frequently recognized novel CTL epitopes include AIIR-ILQQL (SEQ ID NO:1) and ALIRILQQL (SEQ ID NO:2), both of which are restricted by HLA-A*0201 and are located within alpha helix Hα2 domain of Vpr. These peptides represent variants in the Vpr amino acid sequence. The frequency of recognition of these epitope peptides is the same or similar. This region within Vpr is highly conserved and single point mutation, involving either the isoleucin-residue in position 60, that represents the P2 anchor residue for the HLA-*0201-restricted epitope or the C-terminal anchor-residue (position 67) of the novel epitope, have been recently shown to result in a loss of the perinuclear localization of the wild-type protein, indicating the important function of this region.

CTL responses directed against functionally important regions within the virus are more effective immunogens, because CTL-induced viral escape mutations within these domains are less likely to occur or may lead to reduced viral competence. In particular, mutations within Vpr and Vif have been observed in individuals with long-term non-progressive HIV-1 infection and were associated with replication deficient viruses in human and macaque infection.

The accessory HIV-1 proteins Vpr and Vif are frequently targeted by virus-specific CD8+ T cells, whereas Vpu is not or is less frequently targetted. Adapted to the length of the proteins, Vpr was preferentially targeted by HIV-1-specific CD8+ T cells compared to other viral proteins. Despite the small size of these proteins, multiple novel CTL epitopes within Vpr and Vif were defined, several of them located within functionally important sites of these proteins. These novel CTL epitopes represent potential candidates for future HIV-1 vaccines.

Other embodiments are within the following claims.

What is claimed is:

1. A method of inducing an HIV-1 specific cytotoxic T cell immune response, comprising contacting a CD8+ T cell with a polypeptide comprising a frequently-recognized epitope of an HIV-1 accessory protein, wherein said polypeptide comprises an epitope comprising an amino acid sequence of a functionally active domain or a structural domain of said accessory protein and wherein said sequence is SEQ ID NO:2.

2. The method of claim 1, wherein said contacting a CD8+ T cell is performed in the presence of an immunogenicity-enhancing agent.

3. An immunogenic composition comprising a frequently-recognized epitope of an HIV-1 accessory protein, wherein said epitope comprises an amino acid sequence of a functionally active domain or a structural domain of said accessory protein, wherein said epitope comprises the amino acid sequence of SEQ ID NO:2 and further comprising an immunogenicity-enhancing agent.

* * * * *